US009487564B2

(12) United States Patent
Straub et al.

(10) Patent No.: US 9,487,564 B2
(45) Date of Patent: Nov. 8, 2016

(54) FUSOBACTERIUM POLYPEPTIDES AND METHODS OF USE

(75) Inventors: Darren E. Straub, New London, MN (US); Daryll A. Emery, New London, MN (US)

(73) Assignee: EPITOPIX, LLC, Willmar, MN (US)

( * ) Notice: Subject to any disclaimer, the term of this patent is extended or adjusted under 35 U.S.C. 154(b) by 1046 days.

(21) Appl. No.: 12/108,920

(22) Filed: Apr. 24, 2008

(65) Prior Publication Data

US 2008/0199941 A1 Aug. 21, 2008

Related U.S. Application Data

(62) Division of application No. 11/212,115, filed on Aug. 25, 2005.

(60) Provisional application No. 60/604,349, filed on Aug. 25, 2004.

(51) Int. Cl.
| | |
|---|---|
| *C12N 1/00* | (2006.01) |
| *C12N 1/12* | (2006.01) |
| *C07K 1/00* | (2006.01) |
| *C07K 14/00* | (2006.01) |
| *C07K 17/00* | (2006.01) |
| *A61K 39/02* | (2006.01) |
| *A61K 45/00* | (2006.01) |
| *A61K 47/00* | (2006.01) |
| *C07K 14/195* | (2006.01) |
| *C12R 1/01* | (2006.01) |
| *A61K 39/39* | (2006.01) |
| *C12N 1/20* | (2006.01) |
| *A61K 38/00* | (2006.01) |
| *A61K 39/00* | (2006.01) |

(52) U.S. Cl.
CPC .............. *C07K 14/195* (2013.01); *A61K 38/00* (2013.01); *A61K 39/00* (2013.01); *A61K 39/39* (2013.01); *A61K 2039/505* (2013.01); *C12N 1/20* (2013.01); *C12R 1/01* (2013.01)

(58) Field of Classification Search
None
See application file for complete search history.

(56) References Cited

U.S. PATENT DOCUMENTS

| | | | |
|---|---|---|---|
| 5,455,034 A | 10/1995 | Nagaraja et al. | |
| 5,538,733 A | 7/1996 | Emery et al. | |
| 6,027,736 A | 2/2000 | Emery et al. | |
| 6,241,992 B1 | 6/2001 | Morck et al. | |
| 6,632,439 B2 * | 10/2003 | Liem et al. | 424/234.1 |
| 6,669,940 B2 | 12/2003 | Nagaraja et al. | |
| 2003/0206922 A1 | 11/2003 | Emery et al. | |
| 2003/0211118 A1 | 11/2003 | Emery et al. | |
| 2004/0037851 A1 | 2/2004 | Liem et al. | |
| 2004/0047871 A1 * | 3/2004 | Nagaraja et al. | 424/184.1 |
| 2004/0197350 A1 | 10/2004 | Emery et al. | |
| 2004/0197869 A1 | 10/2004 | Emery et al. | |
| 2004/0265329 A1 | 12/2004 | Emery et al. | |
| 2005/0095682 A1 | 5/2005 | Emery et al. | |
| 2005/0186217 A1 | 8/2005 | Straub et al. | |
| 2006/0024323 A1 | 2/2006 | Emery et al. | |
| 2006/0083753 A1 * | 4/2006 | Straub et al. | 424/190.1 |

FOREIGN PATENT DOCUMENTS

| | | |
|---|---|---|
| WO | WO 01/37810 A2 | 5/2001 |
| WO | WO 01/37810 A3 | 5/2001 |

OTHER PUBLICATIONS

Ainsworth et al., (J. Vet Diagn Invest, 1993; 5: 282-283).*
Bakken et al., FEMS Microbiology Immunology, 1989; 47:473-484.*
Bakken et al., Journal of General Microbiology, 1986; 132:1069-1078.*
Harlow et al., Antibodies—A laboratory Manual; Chapter 5, 1988; 66-67.*
Abe et al., "*Fusobacterium necrophorum* Infection in Mice as a Model for the Study of Liver Abscess Formation and Induction of Immunity," *Infect. Immun.*, May 1976; 13(5):1473-1478.
Ainsworth et al., "Outer membrane proteins of *Fusobacterium necrophorum* biovars A, AB, and B: their taxonomic relationship to *F. necrophorum*subspecies *necrophorum* and *F. necrophorum* subspecies funduliforme," *J. Vet. Diagn. Invest.*, Apr. 1993;5(2):282-283.
Bolstad et al., "Molecular characterization of a 40-kDa outer membrane protein, FomA, of *Fusobacterium periodonticum* and comparison with *Fusobacterium nucleatum*," *Oral Microbiol Immunol.*, Oct. 1995; 10(5): 257-264.
Bolstad et al., "Taxonomy, Biology, and Periodontal Aspects of *Fusobacterium nucleatum*," *Clinical Microbiology Reviews*, Jan. 1996; 9(1):55-71.
Conlon et al., "Evaluation of Experimentally Induced *Fusobacterium necrophorum* Infections in Mice," *Infect. Immun.*, Feb. 1977; 15(2):510-517.
Coyle-Dennis et al., "Correlations Between Leukocidin Production and Virulence of Two Isolates of *Fusobacterium necrophorum*," *Am. J. Vet. Res.*, Feb. 1979; 40(2):274-276.
Emery et al., "Generation of Immunity Against *Fusobacterium necrophorum* in Mice Inoculated with Extracts Containing Leucocidin," *Vet. Microbiol.*, Sep. 1986, 12(3): 255-268.

(Continued)

*Primary Examiner* — Gary Nickol
*Assistant Examiner* — Lakia Tongue
(74) *Attorney, Agent, or Firm* — Mueting, Raasch & Gebhardt, PA

(57) ABSTRACT

The present invention provides isolated polypeptides isolatable from a *Fusobacterium* spp. Also provided by the present invention are compositions that include one or more of the polypeptides, and methods for making and methods for using the polypeptides.

7 Claims, 5 Drawing Sheets

(56) References Cited

OTHER PUBLICATIONS

E-Toxate® (Technical Bulletin No. 210). SIGMA Chemical Company, St. Louis, MO, 1998. pp. 1-4.
Garcia et al., "Intraperitoneal Immunization against Necrobacillosis in Experimental Animals," *Can. J. Comp. Med.*, Jan. 1978, 42(1):121-127.
Haake et al., "Cloning and expression of *FOMA*, the Major Outer-Membrane Protein Gene from *Fusobacterium Nucleatum* T18," *Arch Oral Biol.*, Jan. 1997; 42(1): 19-24.
Harlow and Lane, *Antibodies, A Laboratory Manual, Chapter 5*, Cold Spring Harbor Laboratory, Cold Spring Harbor, New York, NY 1988, Title page, Publication page, Table of Contents, and pp. 55-137.
Hauptmeier, "Footrot in Beef Cattle," Iowa Beef Center, Mar. 1997, 2 pgs. (Also available online at http:www.ioawbeef.org/Publications.footrot.pdf.)
Heinrichs et al., "Identification and Characterization of SirA, an Iron-Regulated Protein from *Staphylococcus aureus*," *J. Bacteriol.*, Mar. 1999; 181(5):1436-1443.
Hussain et al., "A Lithium Chloride-Extracted, Broad-Spectrum-Adhesive 42-Kilodalton Protein of *Staphylococcus epidermidis* is Ornithine Carbamoyltransferase," *Infect. Immun.*, Dec. 1999; 67(12):6688-6690.
Kapatral et al., "Genome Analysis of *F. nucleatum* sub spp *vincetii* and Its Comparison With the Genome of *F. nucleatum* ATCC 25586," *Genome Res.*, 2003; 13:1180-1189.
Kapatral et al., "Genome Sequence and Analysis of the Oral Bacterium *Fusobacterium nucleatum* Strain ATCC 25586," *J. Bacteriol.*, Apr. 2002;184(7): 2005-2018.
Keler et al., "Metachromatic Assay for the Quantitative Determination of Bacterial Endotoxins," *Analyt. Biochem.* 1986; 156:189-193.
Kleivdal et al., "Identification of positively charged residues of FomA porin of *Fusobacterium nucleatum* which are important for pore function," *Eur. J. Biochem.*, Mar. 1999; 260(3):818-824.
Kleivdal et al., "The *Fusobacterium nucleatum* major outer-membrane protein (FomA) forms trimeric, water-filled channels in lipid bilayer membranes," *Eur. J. Biochem.*, Oct. 1995; 233(1):310-316.
Kleivdal et al., "Topological investigations of the FomA porin from *Fusobacterium nucleatum* and identification of the constriction loop L6," *Microbiology*, Apr. 2001; 147(4):1059-1067.
Langworth, "*Fusobacterium necrophorum*: Its Characteristics and Role as an Animal Pathogen," *Bacteriol. Rev.*, Jun. 1977;41(2):373-390.
Mandell et al. (Eds.), *Principles and Practice of Infectious Diseases, Second Edition*, John Wiley and Sons, New York, 1979, Title page, Publication page, and pp. 1377-1378.
Narayanan et al., "Cloning, Sequencing, and Expression of the Leukotoxin Gene from *Fusobacterium necrophorum*," *Infect. Immun.*, 2001; 69(9):5447-5455.
Narayanan et al., "*Fusobacterium necrophorum* Leukotxin Induces Activation and Apoptosis of Bovine Leukocytes," *Infect. Immun.*, 2002; 70(8):4609-4620.
Narayanan et al., "Immunogenicity and protective effects of truncated recombinant leukotoxin proteins of *Fusobacterium necrophorum* in mice," *Vet. Micro.*, Jun. 2003, 93(4):335-347.
Nikaido and Vaara, "3. Outer Membrane," In: *Escherichia coli* and *Salmonella typhimurium, Cellular and Molecular Biology*, Neidhardt et al., (eds.) American Society for Microbiology, Washington, D.C., pp. 7-22 (1987).
*Product data sheet*: "Dairy Quality University—VOLAR Use in a Dairy Herd With Footrot" datasheet [online]. Bayer Corporation, Shawnee Mission, KS, 1996 [retrieved on Jul. 8, 2004]. Retrieved from the Internet:<URL:http://dqacenter.org/university/moreinfo/rh48.htm>; 2 pgs.
*Product data sheet*: "Merck Vet. Edition—Liver Abscesses in Cattle: Introduction" datasheet [online]. Merck & Co., Inc., Whitehouse Station, New Jersey, 2003 [retrieved on Jun. 24, 2004]. Retrieved from the Internet:<URL:http://www.merckvetmanual.com/mvm/index.jsp?cfile=htm/bc/23500.htm>; 2 pgs.
*Product data sheet*: "VOLAR®" datasheet [online]. Internet Inc., Millsboro, Delaware, 2004 [retrieved on Jun. 24, 2004]. Retrieved from the Internet: <URL:http://www.compasnac.com/cvp/11/1106/1106221.htm>; 4 pgs.
Puntervoll et al., "Structural characterization of the fusobacterial non-specific porin FomA suggests a 14-stranded topology, unlike the classical porins," *Microbiology*, Nov. 2002: 148(11):3395-3403.
Rae, "Injection Site Reactions," [online]. University of Florida, Department of Animal Sciences, [retrieved on Oct. 16, 2003]. Retrieved from the Internet: <URL:http://www.animal.ufl.edu/extension/beef/documents/short94/rae.htm>. 3 pgs.
Saginala et al., "Effect of *Fusobacterium necrophorum* Leukotoxoid Vaccine on Susceptibility to Experimentally Induced Liver Abscesses on Cattle," *J. Animal Sci.*,1997; 75(4):1160-1166.
Smith et al., "Pathogenicity of *Fusobacterium necrophorum* strains from man and animals," *Epidemiol. Infect.*, Jun. 1993; 110(3):499-506.
Tan et al., "*Fusobacterium Necrophorum* Infections: Virulence Factors, Pathogenic Mechanism and Control Measures," *Vet. Res. Commun.*, 20, 1996, pp. 113-140.
Tan et al., "Factors affecting the leukotoxin activity of *Fusobacterium necrophorum*," *Vet. Microbiol.*, Jul. 1992; 32(1):15-28.
Tan et al., "Purification and quantification of *Fusobacterium necrophorum* leukotoxin by using monoclonal antibodies," *Vet. Microbiol.*, Nov. 1994, 42(23):121-133.
Tan et al., "Purification and quantification of *Fusobacterium necrophorum* leukotoxin by using monoclonal antibodies," *Vet. Res. Commun.*, 42, 1994, pp. 121-133.
Tan et al., "Biological and biochemical characterization of *Fusobacterium necrophorum* leutoxin," *Am. J. Vet. Res. Commun.*, 55, 1994, pp. 515.
Trivier et al., "Influence of iron depletion on growth kinetics, siderophore production, and protein expression of *Staphylococcus aureus*," *FEMS Microbiol. Lett.*, Apr. 1995; 127(3):195-199.
*Endotoxins and Their Detection with the Limulus Amebocyte Lysate Test*, Watson et al. (Eds.), Alan R. Liss, Inc., New York, NY, 1982, Title page, Publication page, and Table of Contents (5 pgs).
International Search Report and Written Opinion for PCT application No. PCT/US2005/030290, Dec. 20, 2005.
International Preliminary Report on Patentability for PCT application No. PCT/US2005/030290, Feb. 28, 2007.
Faraldo-Gomez et al., "Acquisition of Siderophores in Gram-Negative Bacteria," *Nature Reviews Molecular Cell Biology*, Feb. 2003;4:105-116.
Rogers et al., "An aminopeptidase nutritionally important to *Fusobacterium nucleatum*," *Microbiology*, 1998;144:1807-1813.
Bachrach, et al., "Identification of a *Fusobacterium nucleatum* 65 kDa Serine Protease," *Oral Microbiology Immunology*, 2004; 19:155-159.
Kleivdal, et al., "The *Fusobacterium nucleatum* Major Outer-membrane Protein (FomA) Form Trimeric, Water-filled Channels in Lipid Bilayer Membranes," *Eur. J Biochem.*,1995; 233:310-316.
Vasstrand, et al., "Demonstration of Lanthionine as a Natural Constituent of the Peptidoglycan of *Fusobacterium nucleatum*," *Infection and Immunity*, Sep. 1979; 25(3):775-780.
Vasstrand, et al., "Composition of Peptidoglycans in *Bacteroidaceae*: Determination and Distribution of Lanthionine," *Infection and Immunity*, Apr. 1982; 36(1):114-122.

\* cited by examiner

FUSOBACTERIUM POLYPEPTIDES AND METHODS OF USE

CONTINUING APPLICATION DATA

This application is a divisional of application Ser. No. 11/212,115, filed Aug. 25, 2005, (pending), which claims the benefit of U.S. Provisional Application Serial No. 60/604,349, filed Aug. 25, 2004, both of which are incorporated by reference herein.

This application claims the benefit of U.S. Provisional Application Ser. No. 60/604,349, filed Aug. 25, 2004, both of which are incorporated by reference herein.

BACKGROUND

*Fusobacterium* spp. are gram-negative, obligately anaerobic and pleomorphically rod shaped bacterium responsible for a variety of necrotic infections in animals and in humans (Langworth, Bacteriol. Rev., 41, 373-390 (1977)). *Fusobacterium necrophorum* is classified into two subspecies: *F. necrophorum* subsp. *necrophorum* and *F. necrophorum* subsp. *funduliforme* and are responsible for a number of clinical manifestations in various species of animals, such as cattle, sheep, and swine to include; hepatic abscesses, foot rot, laminitis, purulent and interdigital dermatitis, contagious eethyma, necrotic rhinitis, and necrotic laryngitis.

In humans, *F. necrophorum* and *F. nucleatum* are considered to be the most pathogenic and are the causative agent of skin ulcers, peritonsillar abscesses, septic arthritis, Lemierre's syndrome, periodontal diseases and endocarditis. A number of other species of *Fusobacterium* have been implicated as the etiological agent in a variety of diseases, for example, *F. ulcercans* (skin ulcers), *F. russi* (animal bite infections), and *F. varium* (eye infections) (Smith et al., Epidemiol Infect., 110, 499-506 (1993)).

The bacterium produces a number of virulence factors that are responsible for the pathogenesis of the organism, including a potent secreted leukotoxin which has been shown to be specifically toxic to ruminant polymorphonuclear leukocytes (Tan et al., Vet. Res. Commun. 20, 113-140 (1996)). The importance of leukotoxin as an important virulence factor has been well documented. For instance, experiments have indicated a correlation between toxin production and the ability of *F. necrophorum* to induce abscesses in laboratory animals (Coyle et al., Am. J. Vet. Res., 40, 274-276. (1979), and Tan et al., Am. J. Vet. Res., 55, 515. (1994)). Experiments have also shown that non-leukotoxin producing strains are unable to induce foot abscesses in cattle following challenge. It has also been shown that neutralizing antibody produced by an inactivated toxoid derived from leukotoxin reduced infection and liver abscesses in vaccinated cattle.

A number of commercial killed whole cell bacterins have been used to control necrotic infection in farm animals incorporating multiple strains including the most prevalent serotypes such as biotype A (*F. necrophorum* subsp. *necrophorum*). Another approach to vaccine development has been the incorporation of leukotoxin as a toxoid to prevent the pathological effect of the secreted toxin (Saginala et al., J. Anim. Sci., 75, 11601166 (1997)). While conventional vaccines have shown some degree of efficacy in preventing colonization and infection with *F. necrophorum*, adequate protection in cattle is still lacking.

Divalent metal ions such as iron, cobalt, copper, magnesium, manganese, molybdenum, nickel, selenium, and zinc and are trace elements often required for the survival of bacteria infecting both animal and human hosts. These trace metal elements are used by bacteria as cofactors for enzymes that catalyze biochemical reactions for various metabolic pathways required by the organism. The impact of iron on the pathogenesis of bacteria has been studied extensively. Iron is essential for nearly all life and is required for enzymatic and metabolic pathways of organisms at all phylogenic levels.

The ability of *Fusobacterium* to evade the natural defense mechanisms of the vertebrate host depends in part on its ability to obtain host iron, which in turn, directly influences the host-pathogen interaction. Because of iron's essential nature, vertebrate hosts have developed elaborate mechanisms to bind iron in body fluids (e.g., transferrin in blood and lymph fluids and lactoferrin in external secretions). These high affinity iron binding proteins create an iron restricted environment within the host, reducing the level of iron to approximately $10^{-18}$ molar, a concentration too low to support the growth of nearly all bacteria. These iron sequestering mechanisms of the host act as a natural defense mechanism to combat bacterial invasion. To circumvent these iron-restrictive conditions many bacterial species have evolved mechanisms for obtaining iron. The most common mechanisms include the diffusion of soluble iron through porins and specialized transport systems that mediate the uptake of iron by siderophores. This latter system is one of the most common and well-studied mechanisms for iron acquisition and involves the specific chelation of ferric iron by siderophores and the synthesis of their cognate transport systems, which permits the bacteria to continue to replicate and overcome the non-specific defense mechanisms of the host. Continued replication, and thus each step in the infectious process, is ultimately dependent on the ability of the organism to obtain iron from its host.

With so many basic functions relying on the availability of iron, bacteria have evolved a complex regulatory network for acquiring iron under varying physiological conditions. Under anaerobic conditions, iron is present in the soluble ferrous form (Fe II) and can freely diffuse through outer membrane porins into the periplasm. For instance, in *E. coli* the FeoAB transport system present in the cytoplasmic membrane will transport the ferrous iron molecules into the cell cytoplasm. Under aerobic conditions and neutral pH, iron is primarily present in the insoluble ferric form (Fe III) and cannot pass through the outer membrane porins by passive diffusion. Instead, molecules called siderophores are secreted by bacteria, which have a high affinity for ferric iron. The ferric-siderophore complexes are recognized by receptors in the outer membrane, collectively referred to as the TonB-dependent receptors. These receptors, once bound to loaded siderophores, are believed to interact with TonB and its associated proteins localized in the periplasm and cytoplasmic membrane. These protein-protein interactions, though poorly understood, serve to provide the energy necessary to transport the ferri-siderophore complexes across the outer membrane and through the periplasmic space. ABC transport systems present in the cytoplasmic membrane serve to transport the iron-siderophore complexes across the cytoplasmic membrane. Reductase enzymes reduce the ferric iron to its ferrous form, which dissociates it from the siderophore and releases iron into the cell.

Several species of pathogenic bacteria use additional mechanisms to obtain iron from mammalian hosts, including the direct binding of transferrin, heme, and other heme-containing compounds. The receptor proteins that bind these iron-containing molecules most likely rely on the TonB complex for the energy required to transport heme across the outer membrane, similar to the iron-siderophore complexes. Specialized ABC transporters are then used to transport the heme across the cytoplasmic membrane. In addition, some bacteria secrete hemophores, small molecules that can bind heme and present it to receptors on the bacterial cell surface. Several pathogenic species also produce hemolysins, which are toxins that lyse red blood cells, releasing heme and hemoglobin for uptake by the bacteria.

The outer membrane proteins of gram-negative bacteria control the selective permeability of many essential nutrients critical to the survival of bacteria, including all pathogenic bacteria that cause disease in animals and man. This selective permeability of nutrients is controlled by a class of membrane proteins called porins. It now appears that the majority of the outer membrane proteins on the surface of gram-negative bacteria are porins, identified as the general porins (e.g., OmpF), monomeric porins (e.g., OmpA), the specific porins (e.g., the maltose-specific porin LamB) and the TonB-dependent, gated porins (e.g., the siderophore receptor FepA). The porin class of proteins generally share structural features, including the presence of beta-barrels that span the outer membrane.

Little is known regarding the iron-acquisition by *Fusobacterium* spp, and genomic comparisons are difficult since the genome of only one strain of *Fusobacterium nucleatum* have been completely sequenced, *F. nucleatum* strain ATCC 25586 (Kapatral et al., J. Bacteriol., 184, 2005-2018 (2002)). However, this genomic sequence was recently used in a comparison with a partially sequenced genome of *F. nucleatum* subspp. *vincentii* (Kapatral et al., Genome Res., 13, 1180-1189 (2003)) to investigate differences among these two subspecies. The results suggested that there were differences between the two genomes with respect to the iron uptake systems. Although iron transport systems were discovered in both genomes, the genome of strain ATCC 25586 contains three additional iron-specific ABC transport systems. In addition, hemin receptor proteins appear to be encoded by both genomes, but while the subspp. *vincentii* isolate encodes three receptors, the genome of strain ATCC 25586 apparently encodes five such proteins. Furthermore, the feoAB genes, encoding a putative ferrous iron transport system, are only found in the genome of the subspp. vincentii isolate. Since both organisms are obligate anaerobes and ferrous iron is the predominant form of the metal under anaerobic conditions, strain ATCC 25586 may have a second mechanism for uptake of ferrous iron. Given the differences among these two subspecies of *F. nucleatum*, it is likely that there will be many differences among the iron uptake systems between other *Fusobacterium* species. Therefore, the *F. nucleatum* genomic data may not be useful for predicting the presence or absence of iron acquisition systems in other species of *Fusobacterium*.

SUMMARY OF THE INVENTION

The present invention provides a composition including isolated polypeptides isolatable from a *Fusobacterium* spp. At least one of the isolated polypeptides is isolatable from the *Fusobacterium* spp. grown in low iron conditions and not isolatable from the *Fusobacterium* spp. grown in high iron conditions, and may have a molecular weight between 24 kDa and 86 kDa. In some aspects of the invention, the composition further includes a second population of isolated polypeptides isolatable from the *Fusobacterium* spp. grown in low iron conditions, wherein expression of the second population of isolated polypeptides is enhanced at least 10% during growth in low metal conditions. The polypeptides of the second population may have molecular weights between 29 kDa and 144 kDa. The composition may also include a pharmaceutically acceptable carrier.

The present invention also provides methods for treating a subject. In one aspect the method includes administering an effective amount of a composition of the present invention to a subject having or at risk of having an infection caused by a *Fusobacterium* spp. The subject may be a mammal, such as an ungulate, or a human. Examples of ungulates include bovine, ovine, or caprine animals.

Also provided by the present invention are methods for treating a condition caused by a *Fusobacterium* spp. In one aspect, the method includes administering an effective amount of a composition of the present invention to a subject having or at risk of having a condition caused by a *Fusobacterium* spp. The subject may be a mammal, such as an ungulate, or a human. Examples of ungulates include bovine, ovine, or caprine animals.

The present invention provides methods for isolating polypeptides from *Fusobacterium* spp., including providing a culture including a *Fusobacterium* spp., wherein the *Fusobacterium* spp. has been incubated in low metal conditions, disrupting the *Fusobacterium* spp. to result in a mixture including disrupted cell membranes, solubilizing the mixture by adding to the mixture a biological detergent to result in a preparation comprising solubilized and unsolubilized polypeptides, and isolating the unsolubilized polypeptides. Also included in the invention are compositions prepared by these methods.

The present invention also provides an isolated polypeptide isolatable from a *Fusobacterium* spp., wherein the polypeptide is expressed by a *Fusobacterium* spp. at a detectable level during growth under low metal conditions and is not expressed by the *Fusobacterium* spp. at a detectable level during growth in high metal conditions. In another aspect, the isolated polypeptide is expressed by a *Fusobacterium* spp. grown in low iron conditions, wherein expression of the isolated polypeptide is enhanced at least 10% during growth in low metal conditions. In yet another aspect, the isolated polypeptide is expressed at substantially the same amount during growth of the *Fusobacterium* spp. in low metal conditions and in high metal conditions.

Further provided by the invention are compositions including an isolated whole cell preparation of a *Fusobacterium* spp. In one aspect, the cells include a metal regulated polypeptide expressed by the *Fusobacterium* spp. during growth under low metal conditions and not expressed during growth in high metal conditions. In another aspect, the cells include a metal regulated polypeptide expressed by the *Fusobacterium* spp. during growth in high metal conditions and expressed at an enhanced level during growth in low metal conditions. The invention also provides method for making such compositions, including providing a culture including a *Fusobacterium* spp, wherein the *Fusobacterium* spp. has been incubated in low metal conditions, and inactivating the *Fusobacterium* spp. to result in a composition containing inactivated *Fusobacterium* spp. cells.

The present invention also provides methods for detecting antibody, including providing a biological sample comprising antibody, contacting the biological sample with a polypeptide isolatable from a *Fusobacterium* spp. to form a mixture, incubating the mixture, and identifying a polypeptide:antibody complex, wherein the presence of a polypeptide:antibody complex indicates the biological sample comprises antibody that specifically binds to the polypeptide. The polypeptide may be a polypeptide that is expressed by a *Fusobacterium* spp. at a detectable level during growth under low metal conditions and is not expressed by the *Fusobacterium* spp. at a detectable level during growth in high metal conditions, or a polypeptide that is enhanced during growth in low metal conditions.

Also provided is a method for passively immunizing a subject, including administering an effective amount of an antibody to a subject having or at risk of having an infection caused by a *Fusobacterium* spp., wherein the antibody specifically binds a polypeptide isolatable from a *Fusobacterium* spp. The polypeptide may be a polypeptide that is expressed by a *Fusobacterium* spp. at a detectable level during growth under low metal conditions and is not expressed by the *Fusobacterium* spp. at a detectable level during growth in high metal conditions, or a polypeptide that is enhanced during growth in low metal conditions.

DETAILED DESCRIPTION OF PREFERRED EMBODIMENTS OF THE INVENTION

Figure 1:
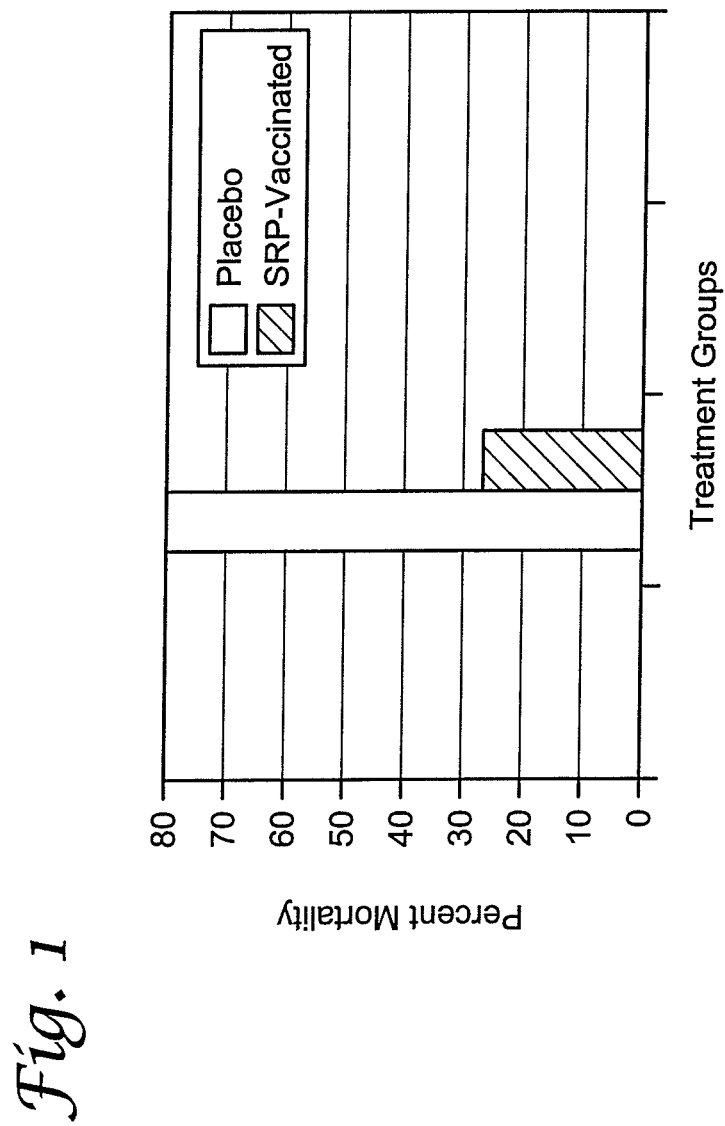
FIG. 1. Differences in mortality between vaccinated and control mice after interperitoneal challenge with *F. necrophorum*.

The present invention provides polypeptides and compositions including one or more of the polypeptides. As used herein, "polypeptide" refers to a polymer of amino acids linked by peptide bonds, and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like. A polypeptide may be isolatable directly from a natural source, or can be prepared with the aid of recombinant, enzymatic, or chemical techniques. In the case of a polypeptide that is naturally occurring, such a polypeptide is typically isolated. An "isolated" polypeptide is one that has been removed from its natural environment. For instance, an "isolated" polypeptide is a polypeptide that has been removed from the cytoplasm or from the outer membrane of a cell, and most of the polypeptides, nucleic acids, and other cellular material of its natural environment are no longer present. An "isolated" polypeptide also includes a polypeptide produced using recombinant techniques, or chemically or enzymatically synthesized. Unless otherwise specified, "a," "an," "the," and "at least one" are used interchangeably and mean one or more than one. The terms "comprises" and variations thereof do not have a limiting meaning where these terms appear in the description and claims.

The polypeptides of the present invention are isolatable from a member of the family Bacteroidaceae, preferably the genus *Fusobacterium*. A member of the genus *Fusobacterium* is also referred to herein as *Fusobacterium* spp. Examples of *Fusobacterium* spp. from which polypeptides of the present invention may be obtained include *F. necrophorum* (including *F. necrophorum* subsp. *necrophorum* and *F. necrophorum* subsp. *funduliforme*), *F. nucleatum*, *F. ulcercans*, *F. russi*, *F. varium*, *F. mortiferum*, *F. gonidiaformans*, and *F. naviforme*. Preferably, the *Fusobacterium* spp. from which polypeptides of the present invention may be obtained is *F. necrophorum*. These microbes are commercially available from a depository such as American Type Culture Collection (ATCC). In addition, such microbes are readily isolatable by isolation techniques known and used in the art. For instance, a microbe may be derived from an infected animal as a field isolate, and used to obtain polypeptides of the present invention as described herein, or stored for future use, for example, in a frozen repository at $-20°$ C. to $-95°$ C., in an appropriate bacteriological media containing 20% glycerol, and other like media. Methods for obtaining the polypeptides from *Fusobacterium* spp. are described herein.

Each polypeptide may be defined by its molecular weight in kilodaltons (kDa). Methods for determining the molecular weight of a polypeptide are routine and known in the art, and include, for instance, gel filtration, gel electrophoresis including sodium dodecyl sulfate (SDS) polyacrylamide gel electrophoresis, capillary electrophoresis, mass spectrometry, and liquid chromatography including HPLC. When the molecular weight of a polypeptide is determined using SDS polyacrylamide gel electrophoresis, conditions appropriate to resolve polypeptides having molecular weights of the polypeptides of the present invention, for instance, between 140 kDa and 30 kDa are used. Such conditions are routine and known to the art.

In one aspect, the polypeptides of the present invention are metal regulated polypeptides. As used herein, a "metal regulated polypeptide" is a polypeptide that is expressed by a member of the genus *Fusobacterium* at a greater level when the microbe is grown in low metal conditions compared to growth of same the microbe in high metal conditions. Metals are those present in the periodic table under Groups 1 through 17 (IUPAC notation; also referred to as Groups I-A, II-A, III-B, IV-B, V-B, VI-B, VII-B, VIII, I-B, II-B, III-A, IV-A, V-A, VI-A, and VII-A, respectively, under CAS notation). Preferably, metals are those in Groups 2 through 12, more preferably, Groups 3-12. Even more preferably, the metal is iron, zinc, copper, magnesium, nickel, cobalt, manganese, molybdenum, or selenium, most preferably, iron.

For instance, one class of metal regulated polypeptide produced by *Fusobacterium* spp. is not expressed at detectable levels during growth of the microbe in high metal conditions but is expressed at detectable levels during growth in low metal conditions. Low metal conditions and high metal conditions are described in greater detail herein. Examples of such metal regulated polypeptides isolatable from a *Fusobacterium* spp. have molecular weights (as determined by separation of the polypeptides using a stacking gel of 4% and a resolving gel of 10% under reducing and denaturing conditions) between 24 kDa and 86 kDa, preferably between 76 kDA and 86 kDa, between 62 kDa and 68 kDa, between 45 kDa and 53 kDa, between 34 kDa and 43 kDa, and between 24 kDa and 35 kDa. More preferably, the metal regulated polypeptides have molecular weights of between 78 kDa and 84 kDa, between 64 kDa and 66 kDa, between 47 kDa and 51 kDa, between 36 kDa and 41 kDa, and between 27 kDa and 32 kDa. Most preferably, the metal regulated polypeptides have molecular weights of 83 kDa, 79 kDa, 65 kDa, 49 kDa, 39 kDa, 38 kDa, 31 kDa, and 28 kDa. Such polypeptides are isolatable from a *Fusobacterium* spp. grown in low iron conditions, and not isolatable from the *Fusobacterium* spp. grown in high iron conditions.

Another type of metal regulated polypeptide produced by *Fusobacterium* spp. is expressed at detectable levels during growth of the microbe in high metal conditions but more of the polypeptide is expressed during growth in low metal conditions. The expression of such polypeptides is referred to herein as "enhanced" during growth in low metal conditions. Typically, the increase in expression of a polypeptide during growth in low metal conditions is between 10% and 50% compared to the expression of the polypeptide during growth in high metal conditions. Examples of metal regulated polypeptides showing enhanced expression and isolatable from *Fusobacterium* spp. have molecular weights (as determined by separation of the polypeptides using an 10% SDS-PAGE gel under reducing and denaturing conditions) between 136 kDA and 144 kDa, between 69 kDa and 77 kDa, between 39 kDa and 47 kDa, and between 29 kDa and 37 kDa. More preferably, the metal regulated polypeptides having enhanced expression have molecular weights of 138 kDa and 142 kDa, between 71 kDa and 75 kDa, between 41 kDa and 45 kDa, and between 31 kDa and 35 kDa. Most preferably, the metal regulated polypeptides having enhanced expression have molecular weights of 140 kDa, 73 kDa, 43 kDa, and 33 kDa.

Whether a metal regulated polypeptide is expressed at a detectable level or has enhanced expression during growth in low metal conditions can be determined by methods useful for comparing the presence of proteins, including, for example, gel filtration, gel electrophoresis including sodium dodecyl sulfate (SDS) polyacrylamide gel electrophoresis, capillary electrophoresis, mass spectrometry, and liquid chromatography including HPLC. Separate cultures of a *Fusobacterium* spp. are grown under high metal conditions and under low metal conditions, polypeptides of the present invention are isolated as described herein, and the polypeptides present in each culture are resolved and compared. Typically, an equal amount of polypeptide from each culture is used. For instance, when SDS polyacrylamide gel electrophoresis is used to compare the polypeptides, 30 μg micrograms of polypeptide from each culture is used and loaded into a well. After running the gel and staining the polypeptides, the two lanes can be compared. A polypeptide that is not expressed at detectable levels during growth is a polypeptide that is undetectable using currently available detection methods, preferably staining with a stain such as Coomasie Brilliant Blue.

In another aspect, the polypeptides of the present invention are not metal regulated and are typically expressed at the same level when the *Fusobacterium* spp. are grown in low metal and high metal conditions. Examples of this type of polypeptide isolatable from *Fusobacterium* spp. have molecular weights (as determined by separation of the polypeptides using a 10% SDS-PAGE gel under reducing and denaturing conditions) between 36 kDA and 45 kDa. More preferably, the molecular weights of this type of polypeptides are 45 kDa, 41 kDa, 40 kDa, and 34 kDa.

Preferably, polypeptides of the present invention have immunogenic activity. "Immunogenic activity" refers to the ability of a polypeptide to elicit an immunological response in an animal. An immunological response to a polypeptide is the development in an animal of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed to an epitope or epitopes of the polypeptide. "Epitope" refers to the site on an antigen to which specific B cells and/or T cells respond so that antibody is produced.

Also provided by the present invention are whole cell preparations of a *Fusobacterium* spp., where the *Fusobacterium* spp. expresses one or more of the polypeptides of the present invention. The cells present in a whole cell preparation are preferably inactivated such that the cells cannot replicate, but the immunogenicity of the polypeptides of the present invention expressed by the *Fusobacterium* spp. is maintained. Typically, the cells are killed by exposure to agents such as glutaraldehyde, formalin, or formaldehyde.

The present invention also provides compositions including at least 1 of the polypeptides of the present invention, more preferably at least 2, at least 3, at least 4, and so on, to at least 14 polypeptides of the present invention. A composition can include polypeptides isolatable from 1 species of *Fusobacterium*, or can be isolatable from a combination of 2 or more species of *Fusobacterium*, for instance, *F. necrophorum* and *F. nucleatum*. Furthermore, a composition can include polypeptides isolatable from 2 or more strains of the same species of *Fusobacterium*. For instance, a composition can include polypeptides isolatable from 2 different isolates of *F. necrophorum* subsp. *necrophorum*. The present invention also provides compositions including a whole cell preparation of at least 1 *Fusobacterium* spp., 2, 3, 4, 5, or 6 *Fusobacterium* spp.

Optionally, a polypeptide of the present invention can be covalently bound to a carrier polypeptide to improve the immunological properties of the polypeptide. Useful carrier polypeptides are known to the art, and include, for instance, leukotoxin derived from *Fusobacterium* spp. The chemical coupling of a polypeptide of the present invention can be carried out using known and routine methods. For instance, various homobifunctional and/or heterobifunctional cross-linker reagents such as bis(sulfosuccinimidyl) suberate, bis (diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-maleimidobenzoyl-N-hydroxysuccinimide, sulfosuccinimidyl 4-(N-maleimidomethyl)cycloheane-1-carboxylate, sulfosuccinimidyl 4-(p-maleimido-phenyl)butyrate and (1-ethyl-3-(dimethyl-aminopropyl) carbodiimide can be used (Harlow and Lane, Antibodies, A Laboratory Manual, generally and Chapter 5, Cold Spring Harbor Laboratory, Cold Spring Harbor, N.Y., N.Y. (1988)).

Preferably, such compositions of the present invention include low concentrations of lipopolysaccharide (LPS). LPS is a component of the outer membrane of most gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp. 7-22 (1987), and typically includes polysaccharides (0-specific chain, the outer and inner core) and the lipid A region. The lipid A component of LPS is the most biologically active component of the LPS structure and together induces a wide spectrum of pathophysiological effects in mammals. The most dramatic effects are fever, disseminated intravascular coagulation, complement activation, hypotensive shock, and death. The non-specific immunostimulatory activity of LPS can enhance the formation of a granuloma at the site of administration of compositions that include LPS. Such reactions can result in undue stress on the animal by which the animal may back off feed or water for a period of time, and exasperate infectious conditions in the animal. In addition, the formation of a granuloma at the site of injection can increase the likelihood of possible down grading of the carcass due to scaring or blemishes of the tissue at the injection site (see, for instance, Rae, Injection Site Reactions, which is available through the website maintained by the Department of Animal Sciences of the University of Florida, Gainesville, FL).

The concentration of LPS can be determined using routine methods known to the art. Such methods typically include measurement of dye binding by LPS (see, for instance, Keler and Nowotny, *Analyt. Biochem.*, 156, 189 (1986)) or the use of a *Limulus amebocyte* lysate (LAL) test (see, for instance, Endotoxins and Their Detection With the *Limulus Amebocyte* Lystate Test, Alan R. Liss, Inc., 150 Fifth Avenue, New York, N.Y. (1982)). There are four basic commercially available methods that are typically used with an LAL test: the gel-clot test; the turbidimetric (spectrophotometric) test; the colorimetric test; and the chromogenic test. An example of a gel-clot assay is available under the tradename E-TOX-ATE (Sigma Chemical Co., St. Louis, Mo.; see Sigma Technical Bulletin No. 210), and PYROTELL (Associates of Cape Cod, Inc., East Falmouth, Mass.). Typically, assay conditions include contacting the composition with a preparation containing a lysate of the circulating amebocytes of the horseshoe crab, *Limulus polyphemus*. When exposed to LPS, the lysate increases in opacity as well as viscosity and may gel. About 0.1 milliliter of the composition is added to lysate. Typically, the pH of the composition is between 6 and 8, preferably, between 6.8 and 7.5. The mixture of composition and lysate is incubated for 1 hour undisturbed at 37° C. After incubation, the mixture is observed to determine if there was gelation of the mixture. Gelation indicates the presence of endotoxin. To determine the amount of endotoxin present in the composition, dilutions of a standardized solution of endotoxin are made and tested at the same time that the composition is tested. Standardized solutions of endotoxin are commercially available from, for instance, Sigma Chemical (Catalog No. 210-SE), U.S. Pharmacopeia (Rockville, Md., Catalog No. 235503), and Associates of Cape Cod, Inc., (Catalog No. E0005). In general, when a composition of the present invention is prepared by isolating polypeptides from a *Fusobacterium* spp. by a method as described herein (e.g., a method that includes disrupting and solubilizing the cells, and collecting the insoluble polypeptides), the amount of LPS in a composition of the present invention is less than the amount of LPS present in a mixture of same amount of the *Fusobacterium* spp. that has been disrupted under the same conditions but not solubilized. Typically, the level of LPS in a composition of the present invention is decreased by, in increasing order of preference, at least 50%, at least 60%, at least 70%, at least 80%, or at least 90% relative to the level of LPS in a composition prepared by disrupting, but not solubilizing, the same *Fusobacterium* spp.

In some aspects, a composition of the present invention does not include a leukotoxin isolatable from a *Fusobacterium* spp. Leukotoxins that are optionally not present in a composition of the present invention include polypeptides having a molecular weight of 300 kDa based on analysis with a 10% SDS-PAGE gel under reducing and denaturing conditions, and having an activity that is toxic to bovine leukocytes (Narayanan et al., Infect. Imun. 69, 5447-5455 (2001), and Narayanan et al., Infect. Immun., 70, 4609-4620 (2002)). Whether a polypeptide has leukotoxin activity can be determined using the monoclonal antibody F7B10 which is reactive against a *F. necrophorum* leukotoxin (Tan et al., Vet. Microbiol., 42, 121-133 (1994), or by determining whether the polypeptide is toxic to ruminant leukocytes. Methods for measuring the toxicity of a polypeptide for ruminant leukocytes are known in the art (Narayanan et al., Infect. Imun., 69, 5447-5455 (2001), and Narayanan et al., Infect. Immun., 70, 4609-4620 (2002).

The compositions of the present invention optionally further include a pharmaceutically acceptable carrier. "Pharmaceutically acceptable" refers to a diluent, carrier, excipient, salt, etc., that is compatible with the other ingredients of the composition, and not deleterious to the recipient thereof. Typically, the composition includes a pharmaceutically acceptable carrier when the composition is used as described herein. The compositions of the present invention may be formulated in pharmaceutical preparations in a variety of forms adapted to the chosen route of administration, preferably, routes suitable for stimulating an immune response to an antigen. Thus, a composition of the present invention can be administered via known routes including, for example, oral; parental including intradermal, subcutaneous, intramuscular, intravenous, intraperitoneal, etc., and topically, such as, intranasal, intrapulmonary, intramammary, intravaginal, intrauterine, intradermal, and rectally etc. It is foreseen that a composition can be administered to a mucosal surface, such as by administration to the nasal or respiratory mucosa (e.g. spray or aerosol), to stimulate mucosal immunity, such as production of secretory IgA antibodies, throughout the animal's body.

A composition of the present invention can also be administered via a sustained or delayed release implant, including biodegradable and/or erodable implants. Suitable implants are known. Some examples of implants suitable for use according to the invention are disclosed in Emery and Straub (WO 01/37810). Implants can be produced at sizes small enough to be administered by aerosol or spray. Implants also include nanospheres and microspheres.

A composition of the present invention is administered in an amount sufficient to provide an immunological response to polypeptides or whole cells of the present invention present in the composition. The amount of polypeptide present in a composition of the present invention can vary. For instance, the dosage of polypeptide can be between 0.01 micrograms (µg) and 3000 milligrams (mg), typically between 10 mg and 2000 mg. When the composition is a whole cell preparation, the cells can be present at a concentration of $10^6$ bacteria/ml, $10^7$ bacteria/ml, $10^8$ bacteria/ml, or $10^9$ bacteria/ml. For an injectable composition (e.g. subcutaneous, intramuscular, etc.) the polypeptide is preferably present in the composition in an amount such that the total volume of the composition administered is 0.5 ml to 5.0 ml, typically 1.0-3.0 ml. When the composition is a whole cell preparation, the cells are preferably present in the composition in an amount that the total volume of the composition administered is 0.5 ml to 5.0 ml, typically 1.0-2.0 ml. The amount administered will vary depending on various factors including, but not limited to, the specific polypeptides or cells chosen, the weight, physical condition and age of the animal, and the route of administration. Thus, the absolute weight of the polypeptide or number of cells included in a given unit dosage form can vary, and depends upon factors such as the species, age, weight and physical condition of the animal, as well as the method of administration. Such factors can be determined by one skilled in the art. Other examples of dosages suitable for the invention are disclosed in Emery et al. (U.S. Pat. No. 6,027,736).

The formulations may be conveniently presented in unit dosage form and may be prepared by methods well known in the art of pharmacy. All methods of preparing a composition including a pharmaceutically acceptable carrier include the step of bringing the active compound (e.g., a polypeptide or whole cell of the present invention) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition including a pharmaceutically acceptable carrier can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyldioctadecylammonium bromide (DDA), pyridine, aluminum hydroxide, oils, saponins, alpha-tocopherol, polysaccharides, emulsified paraffins (available from under the tradename EMULSIGEN from MVP Laboratories, Ralston, Nebr.), ISA-70, RIBI and other substances known in the art.

In another embodiment, a composition of the invention including a pharmaceutically acceptable carrier can include a biological response modifier, such as, for example, IL-2, IL-4 and/or IL-6, TNF, IFN-alpha, IFN-gamma, and other cytokines that effect immune cells. A composition can also include an antibiotic, preservative, anti-oxidant, chelating agent, etc. Such components are known in the art.

Polypeptides and whole cell preparations of the present invention may be obtained by incubating a member of the genus *Fusobacterium* under conditions that promote expression of one or more of the polypeptides described herein. The present invention also includes compositions prepared by the processes disclosed herein. Typically, such conditions are low metal conditions. As used herein, the phrase "low metal conditions" refers to an environment, typically bacteriological media, that contains amounts of a free metal that cause a microbe to express metal regulated polypeptides. As used herein, the phrase "high metal conditions" refers to an environment that contains amounts of a free metal that cause a microbe to either not express one or more of the metal regulated polypeptides described herein, or to decrease expression of such a polypeptide. Low metal conditions are generally the result of the addition of a metal chelating compound to a bacteriological medium. High metal conditions are generally present when a chelator is not present in the medium, and/or a metal is added to the medium. Examples of metal chelators include natural and synthetic compounds. Examples of natural compounds include plant phenolic compounds, such as flavonoids. Examples of flavinoids include the copper chelators catechin and naringenin, and the iron chelators myricetin and quercetin. Examples of synthetic copper chelators include, for instance, tetrathiomolybdate, and examples of synthetic zinc chelators include, for instance, N,N,N',N'-Tetrakis (2-pyridylmethyl)-ethylene diamine. Examples of synthetic iron chelators include 2,2'-dipyridyl (also referred to in the art as α,α'-bipyridyl), 8-hydroxyquinoline, ethylenediamine-di-O-hydroxyphenylacetic acid (EDDHA), desferrioxamine methanesulphonate (desferol), transferrin, lactoferrin, ovotransferrin, biological siderophores, such as, the catecholates and hydroxamates, and citrate. Preferably, 2,2'-dipyridyl is used for the chelation of iron. Typically, 2,2'-dipyridyl is added to the media at a concentration of at least 0.0025 micrograms/milliliter (μg/ml), at least 0.025 μg/ml, or at least 0.25 μg/ml. High levels of 2,2'-dipyridyl can be 10 μg/ml, 20 μg/ml, or 30 μg/ml.

It is expected that a *Fusobacterium* spp. with a mutation in a fur gene will result in the constitutive expression of many, if not all, of the metal regulated polypeptides of the present invention. A potential fur gene has been identified in a *F. nucleatum* (Kapatral et al., J. Bacteriol. 184 (7), 2005-2018 (2002)). The production of a fur mutation in a *Fusobacterium* spp. can be produced using routine methods including, for instance, electroporation and genetic constructs useful for gene knock-out in gram negative bacteria.

Many *Fusobacterium* spp. are able to grow in low metal conditions in vitro in artificial media only after adaptation. For instance, a *Fusobacterium* spp. can be adapted to low iron conditions in vitro by growth in the presence of low concentrations of an iron chelator and, after growth in a medium containing the chelator, gradually increasing the concentration of the chelator. For instance, a *Fusobacterium* spp. can be adapted to growth in low iron conditions by adding 0.0025 μg/ml of 2,2'-dipyridyl to a medium, and gradually increasing the concentration of the chelator to a greater concentration, for instance 20 μg/ml.

The medium used to incubate the microbe is not critical, and the volume of medium used to incubate the microbe can vary. When a *Fusobacterium* spp. microbe is being evaluated for the ability to produce the polypeptides described herein, the microbe can be grown in a suitable volume, for instance, 10 milliliters to 1 liter of medium. When a microbe is being grown to obtain polypeptides for use in, for instance, administration to animals, the microbe may be grown in a fermentor to allow the isolation of larger amounts of polypeptides. Methods for growing microbes in a fermentor are routine and known to the art. The conditions used for growing a microbe preferably include a metal chelator, more preferably an iron chelator, for instance 2,2'-dipyridyl, a pH of between 6.5 and 7.5, preferably between 6.9 and 7.1, and a temperature of 37° C. When a fermentor is used, the culture may be purged with an appropriate gas, for instance, nitrogen, to maintain anaerobic conditions. Members of the genus *Fusobacterium* are obligate anaerobes, thus growth conditions do not include levels of oxygen that will prevent growth.

In some aspects of the invention, a *Fusobacterium* spp. may be harvested after growth. Harvesting includes concentrating the microbe into a smaller volume and suspending in a media different than the growth media. Methods for concentrating a microbe are routine and known to the art, and include, for example, filtration and/or centrifugation. Typically, the concentrated microbe is suspended in decreasing amounts of buffer. Preferably, the final buffer includes a metal chelator, preferably, ethylenediaminetetraacetic acid (EDTA). An example of a buffer that can be used contains Tris-base (7.3 grams/liter) and EDTA (0.9 grams/liter), at a pH of 8.5. Optionally, the final buffer also minimizes proteolytic degradation. This can be accomplished by having the final buffer at a pH of greater than 8.0, preferably, at least 8.5, and/or including one or more proteinase inhibitors (e.g., phenylmethanesulfonyl fluoride). Optionally and preferably, the concentrated microbe is frozen at −20° C. or below until disrupted.

When the *Fusobacterium* spp. is to be used as a whole cell preparation, the harvested cells may be processed using routine and known methods to inactivate the cells. Alternatively, when a *Fusobacterium* spp. is to be used to prepare polypeptides of the present invention, the *Fusobacterium* spp. may be disrupted using chemical, physical, or mechanical methods routine and known to the art, including, for example, french press, sonication, or homogenization. Preferably, homogenization is used. As used herein, "disruption" refers to the breaking up of the cell. Disruption of a microbe can be measured by methods that are routine and known to the art, including, for instance, changes in optical density. Typically, a microbe is subjected to disruption until the percent transmittance is increased by 20% when a 1:100 dilution is measured. The temperature during disruption is typically kept at 4° C., to further minimize proteolytic degradation.

The disrupted microbe is solubilized in a detergent, for instance, an anionic, zwitterionic, nonionic, or cationic detergent. Preferably, the detergent is sarcosine, more preferably, sodium lauroyl sarcosinate. As used herein, the term "solubilize" refers to dissolving cellular materials (e.g., polypeptides, nucleic acids, carbohydrates) into the aqueous phase of the buffer in which the microbe was disrupted, and the formation of aggregates of insoluble cellular materials. The conditions for solubilization preferably result in the aggregation of polypeptides of the present invention into insoluble aggregates that are large enough to allow easy isolation by, for instance, centrifugation.

Preferably, the sarcosine is added such that the final ratio of sarcosine to gram weight of disrupted microbe is between 1.0 gram sarcosine per 4.5 grams pellet mass and 6.0 grams sarcosine per 4.5 grams pellet mass, preferably, 4.5 gram sarcosine per 4.5 grams pellet mass. The solubilization of the microbe may be measured by methods that are routine and known to the art, including, for instance, changes in optical density. Typically, the solubilization is allowed to occur for at least 24 hours, more preferably, at least 48 hours, most preferably, at least 60 hours. The temperature during disruption is typically kept low, preferably at 4° C.

The insoluble aggregates that include the polypeptides of the present invention may be isolated by methods that are routine and known to the art. Preferably, the insoluble aggregates are isolated by centrifugation. Typically, centrifugation of outer membrane polypeptides that are insoluble in detergents requires centrifugal forces of at least 50,000×g, typically 100,000×g. The use of such centrifugal forces requires the use of ultracentrifuges, and scale-up to process large volumes of sample is often difficult and not economical with these types of centrifuges. The methods described herein provide for the production of insoluble aggregates large enough to allow the use of significantly lower centrifugal forces (for instance, 46,000×g). Methods for processing large volumes at these lower centrifugal forces are available and known to the art. Thus, the insoluble aggregates can be isolated at a significantly lower cost.

Optionally and preferably, the sarcosine is removed from the isolated polypeptides. Methods for removing sarcosine from the isolated polypeptides are known to the art, and include, for instance, diafiltration, precipitation, hydrophobic chromatography, ion-exchange chromatography, and/or affinity chromatography, and ultra filtration and washing the polypeptides in alcohol by diafiltration. After isolation, the polypeptides suspended in buffer and stored at low temperature, for instance, −20° C. or below.

Polypeptides of the present invention may also be isolated from *Fusobacterium* spp. using methods that are known to the art. The isolation of the polypeptides may be accomplished as described in, for instance, Hussain, et al. *Infect. Immun.*, 67, 6688-6690 (1999); Trivier, et al., *FEMS Microbiol. Lett.*, 127, 195-199 (1995); Heinrichs, et al., *J. Bacteriol.*, 181, 1436-1443 (1999).

In those aspects of the present invention where a whole cell preparation is to be made, after growth of a *Fusobacterium* spp. the microbe can be killed with the addition of an agent such as glutaraldehyde, formalin, or formaldehyde, at a concentration sufficient to inactivate the cells in the culture. For instance, formalin can be added at a concentration of 3% (vol:vol). After a period of time sufficient to inactivate the cells, the cells can be harvested by, for instance, diafiltration and/or centrifugation, and washed.

An aspect of the present invention is further directed to methods of using the compositions of the present invention. The methods include administering to an animal an effective amount of a composition of the present invention. Preferably, the composition further includes a pharmaceutically acceptable carrier. As used herein, an "effective amount" of a composition of the present invention is the amount able to elicit the desired response in the recipient. The composition can be administered at a time that maternal antibody may be present, for instance, as early as one day of age, or at a later time during the life of the animal. The animal can be, for instance, an ungulate, a companion animal, or a human. Examples of ungulates include animals that are bovine (including, for instance, cattle), caprine (including, for instance, goats), ovine (including, for instance, sheep), porcine (including, for instance, swine), equine (including, for instance, horses), members of the family Cervidae (including, for instance, deer, elk, moose, caribou and reindeer), and Bison (including, for instance, buffalo). Examples of companion animals include dogs and cats.

In some aspects, the methods may further include additional administrations (e.g., one or more booster administrations) of the composition to the animal to enhance or stimulate a secondary immune response. A booster can be administered at a time after the first administration, for instance, 1 to 8 weeks, preferably 2 to 4 weeks, after the first administration of the composition. Subsequent boosters can be administered one, two, three, four, or more times annually. Without intending to be limited by theory, it is expected that annual boosters will not be necessary, as an animal will be challenged in the field by exposure to members of the genus *Fusobacterium* expressing polypeptides having epitopes that are identical to or structurally related to epitopes present on the polypeptides present in the composition administered to the animal.

In one aspect, the invention is directed to methods for making antibody to a polypeptide of the present invention, for instance, by inducing the production of antibody in an animal, or by recombinant techniques. The antibody produced includes antibody that specifically binds at least one polypeptide present in the composition. In this aspect of the invention, an "effective amount" is an amount effective to result in the production of antibody in the animal. Methods for determining whether an animal has produced antibodies that specifically bind polypeptides present in a composition of the present invention can be determined as described herein. As used herein, an antibody that can "specifically bind" a polypeptide is an antibody that interacts only with the epitope of the antigen that induced the synthesis of the antibody, or interacts with a structurally related epitope. An antibody that "specifically binds" to an epitope will, under the appropriate conditions, interact with the epitope even in the presence of a diversity of potential binding targets.

In one aspect the invention is also directed to treating an infection in an animal caused by a member of the genus *Fusobacterium*. The infection may be caused exclusively by *Fusobacterium* spp., or may be a mixed infection of *Fusobacterium* spp. and, for instance, *Bacteriodes nodoses*. The method includes administering an effective amount of the composition of the present invention to an animal having an infection caused by a member of the genus *Fusobacterium*, and determining whether the *Fusobacterium* spp. causing the infection has decreased. Methods for determining whether an infection is caused by a member of the genus *Fusobacterium* are routine and known to the art. It is expected that compositions made with polypeptides isolatable from one species of *Fusobacterium* will be useful in the methods described herein against other species of *Fusobacterium*.

In another aspect, the present invention is directed to methods for treating one or more symptoms of certain conditions in animals that may be caused by infection by a member of the genus *Fusobacterium*. Examples of conditions caused by *Fusobacterium* spp. infections include hepatic abscesses, foot rot, laminitis, purulent dermatitis, interdigital dermatitis, contagious ecthyma, necrotic rhinitis, skin ulcers, peritonsillar abscesses, septic arthritis, Lemierre's syndrome, and endocarditis. Treatment of these conditions can be prophylactic or, alternatively, can be initiated after the development of a condition described herein. Treatment that is prophylactic, for instance, initiated before a subject manifests symptoms of a condition caused by *Fusobacterium* spp., is referred to herein as treatment of a subject that is "at risk" of developing the condition. Typically, an animal "at risk" of developing a condition is an animal likely to be exposed to a *Fusobacterium* spp. causing the condition. For instance, the animal is present in an area where the condition has been diagnosed in at least one other animal, or is being transported to an area where a *Fusobacterium* spp. is endemic, and/or where conditions caused by *Fusobacterium* spp. are prevalent. Accordingly, administration of a composition can be performed before, during, or after the occurrence of the conditions described herein. Treatment initiated after the development of a condition may result in decreasing the severity of the symptoms of one of the conditions, including completely removing the symptoms. In this aspect of the invention, an "effective amount" is an amount effective to prevent the manifestation of symptoms of a condition, decrease the severity of the symptoms of a condition, and/or completely remove the symptoms. The potency of a composition of the present invention can be tested according to standard methods. For instance, the use of mice as an experimental model for *Fusobacterium* spp. infection in humans and large animals such as cattle is well established (Conion et al, Infect. Immun, 15, 510-517 (1977), Garcia and McKay, Can. J. Comp. Med, 42, 121-127 (1978), Abe et al., Infect. Immun, 13, 1473-1478 (1976), Emery and Vaughan, Vet. Microbiol, 12, 255-268 (1986). Smith et al., Epidemiol. Infect, 110, 499-506 (1993), and Narayanan et al. Vet. Micro. 93, 335-347 (2003)). The mouse model has proven to be a valuable model to evaluate the immunogenicity and identification of various target antigens provided by various *Fusobacterium* species. Alternatively, when the condition is present in an animal such as, for instance, a sheep or cow, a controlled experimental trial can be run by vaccinating animals with varying levels of the composition and challenging vaccinated and unvaccinated animals with a *Fusobacterium* spp. Methods for determining whether an animal has the conditions disclosed herein and symptoms associated with the conditions are routine and known to the art. Symptoms often associated with hepatic abscesses can be a range of pathologies, from small foci of lymphocyte inflammation surrounded by low numbers of degenerating hepatcytes, to pronounced foci with necrosis and hemorrhage, loss of hepatocytes, fibrin and mixed inflammatory cells at the margin of the necrotic area.

A composition of the invention can be used to provide for passive immunization against infection by *Fusobacterium* spp. For instance, the composition can be administered to an animal to induce the production of immune products, such as antibodies, which can be collected from the producing animal and administered to another animal to provide passive immunity. Immune components, such as antibodies, can be collected to prepare antibody compositions from serum, plasma, blood, colostrum, etc. for passive immunization therapies. Antibody compositions including monoclonal antibodies, anti-idiotypes, and/or recombinant antibodies can also be prepared using known methods. Passive antibody compositions and fragments thereof, e.g., scFv, Fab, $F(ab')_2$ or Fv or other modified forms thereof, may be administered to a recipient in the form of serum, plasma, blood, colostrum, and the like. However, the antibodies may also be isolated from serum, plasma, blood, colostrum, and the like, using known methods and spray dried or lyophilized for later use in a concentrated or reconstituted form. Passive immunizing preparations may be particularly advantageous for treatment of acute systemic illness, or passive immunization of young animals that failed to receive adequate levels of passive immunity through maternal colostrum.

Another aspect of the present invention provides methods for detecting antibody that specifically binds polypeptides of the present invention. These methods are useful in, for instance, detecting whether an animal has antibody that specifically binds polypeptides of the present invention, and diagnosing whether an animal may have an infection caused by *Fusobacterium* spp. Preferably, such diagnostic systems are in kit form. The methods include contacting an antibody with a preparation that includes at least one polypeptide of the present invention to result in a mixture. Preferably, the antibody is present in a biological sample, more preferably blood, milk, or colostrum. The method further includes incubating the mixture under conditions to allow the antibody to specifically bind a polypeptide to form a polypeptide:antibody complex. As used herein, the term "polypeptide:antibody complex" refers to the complex that results when an antibody specifically binds to a polypeptide. The preparation that includes the polypeptides present in a composition of the present invention may also include reagents, for instance a buffer, that provide conditions appropriate for the formation of the polypeptide:antibody complex. The polypeptide:antibody complex is then detected. The detection of antibodies is known in the art and can include, for instance, immunofluorescence and peroxidase.

The methods for detecting the presence of antibodies that specifically bind to polypeptides of the present invention can be used in various formats that have been used to detect antibody, including radioimmunoassay and enzyme-linked immunosorbent assay.

The present invention also provides a kit for detecting antibody that specifically binds polypeptides of the present invention. The kit includes at least one polypeptide of the present invention in a suitable packaging material in an amount sufficient for at least one assay. Optionally, other reagents such as buffers and solutions needed to practice the invention are also included. Instructions for use of the packaged polypeptides are also typically included.

As used herein, the phrase "packaging material" refers to one or more physical structures used to house the contents of the kit. The packaging material is constructed by known methods, preferably to provide a sterile, contaminant-free environment. The packaging material has a label which indicates that the polypeptides can be used for detecting antibodies induced by infection with *Fusobacterium* spp. In addition, the packaging material contains instructions indicating how the materials within the kit are employed to detect such antibodies. As used herein, the term "package" refers to a solid matrix or material such as glass, plastic, paper, foil, and the like, capable of holding within fixed limits the polypeptides. Thus, for example, a package can be a microtiter plate well to which microgram quantities of polypeptides have been affixed. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

EXAMPLES

Example 1

*Fusobacterium* spp. Culture Conditions

*Fusobacterium* spp. *necrophorum* can be grown under controlled fermentation conditions so as to express proteins, including proteins associated with the outer membrane. The bacteria can be harvested and the proteins can then be isolated and used as immunogens in a composition.

Anaerobic conditions for growth of *F. necrophorum* on plates and in small liquid cultures were established by incubation in an anaerobic jar containing an anaerobic gas generator system. A master seed stock of a *Fusobacterium necrophorum* subsp. *necrophorum* originating from a sheep deposited with the American Type Culture Collection, Manassas, VA on Sep. 16, 2009 and given ATCC Accession No. PTA-10318) was prepared by inoculating the isolate into 200 ml of Porcine Brain Heart Infusion Broth (P-BHI, Difco) containing 0.05% cysteine (Sigma) and containing 15 to 20 micrograms per milliliter (μg/ml) of 2,2-dipyridyl (Sigma-Aldrich St. Louis, MO). The culture was grown without stirring at 16 hours at 37° C. under anaerobic conditions. Prior to growth in a starter culture, the *F. necrophorum* subsp. necrophorum was adapted to grow in the iron chelator 2,2-dipyridyl by repeatedly sub-culturing the isolate into increasing concentrations of the iron chelator, beginning at 0.0025 pg/ml, and increasing to 20μg/ml. The bacteria were collected by centrifugation at 10,000 x g. The bacterial pellet was resuspended into 20 ml P-BHI containing 20% glycerol, and sterilely dispensed into 2 ml cryogenic vials (1 ml per vial) and stored at -90° C. The isolate was given the identification number MS 040525, and established as a master seed. The master seed was expanded into a working seed that was then used for the production of metal regulated proteins.

Example 2

Production of Metal Regulated Proteins

Fermentation: A cryogenic vial of the working seed (1 ml at $10^9$ CFU/ml) was used to inoculate 130 ml of 37° C. P-BHI containing 15 micrograms (μg) 2,2-dipyridyl and 0.05% cysteine (Sigma) and incubated in a candle jar. The culture was incubated at 37° C. for 12 hours at which point was sterilely transferred into 1.3 liters of the above media. This second culture was allowed to grow for an additional 10 hours at 37° C. This culture was used to inoculate a 20-liter BIOFLO IV bench-top fermentor, (New Brunswick Scientific Co, Edison NJ) charged with 13 liters of the above-described media. The pH was held constant between 6.9 and 7.1 by automatic titration with 30% NaOH and 10% HCL. The stirring speed was adjusted to 100 revolutions per minute (rpm), and the culture purged with pure nitrogen to maintain an anaerobic condition. The culture was allowed to grow continuously at these conditions for 24 hours at which point the fermentation was terminated by lowing the temperature of the fermentor to 10° C.

Harvest: The bacterial fermentation was concentrated and washed using a MILLIPORE PELLICON Tangential Flow Filter assembly (Millipore Corporation, Bedford, MA), equipped with a 25ft$^2$ screen-channel series ALPHA 300K CENTRASETTE filter (Pall Filtron). The original culture volume of 13 liters was reduced to 2.5 liters. The bacterial retentate was then adjusted to 25 liters using physiological saline (0.85%) and then concentrated again to 2.5 liters to help remove any contaminates not associated with the cells, e.g., secreted proteins. The retentate (2.5 liters) was adjusted to 15 liters using sterile Osmotic Shock Buffer (OMS) containing 7.26 grams/liter Tris-base and 0.93 grams/liter EDTA adjusted to a pH of 8.5. The retentate was mixed thoroughly and equally dispensed (3.0 liters each) into 5 sterile four liter NALGENE containers and placed into a -20° C. freezer for storage. The pellet mass was calculated by centrifuging 30 ml samples of the fermented culture and final harvest. Briefly, pre-weighted 50 ml NALGENE conical tubes were centrifuged at 39,000 x g for 90 minutes in a BECKMAN J2-21 centrifuge using a JA-21 rotor (Beckman Instruments, Palo Alto, CA). At the end of the run, the supernate was poured off and the tubes were weighed again. The pellet mass was calculated for each stage.

Disruption (Homogenization): Three liters of frozen bacterial cell slurry in OMS was thawed at 4° C. (180 gram pellet mass). The liquid culture suspension was aseptically transferred into a 50 liter jacketed process tank containing 44 liters OMS pH 8.5 containing 0.1 grams thimerosal/liter as preservative. The bulk bacterial suspension was chilled to 4° C. with continuous mixing for 18 hours at 200 rpm at which time was disrupted by homogenization. Briefly, the 50 liter tank containing the bacterial suspension was connected to a model 12.51 H RANNIE Homogenizer, (APV Systems, Rosemont, IL). A second 50 liter jacketed process tank (empty) was connected to the homogenizer such that the fluid in the process tank could be passed through the homogenizer, into the empty tank and back again, allowing for multiple homogenizing passes while still maintaining a closed system. The temperature during homogenization was kept at 4° C. At the start of each pass, fluid was circulated at 70 psi through the homogenizer and back to the tank of origin, while the homogenizer pressure was adjusted to 13,500 psi. Prior to the first pass, two pre-homogenizing samples were withdrawn from the homogenizer to establish a baseline for determining the degree of disruption and monitoring of pH. The degree of disruption was monitored by transmittance (%T at 540nanometers (nm) at 1:100 dilution) compared to the non-homogenized sample. The bacterial suspension was passed three times through the homogenizer to give a final percent transmittance between 78-83%T at a 1:100 dilution.

After homogenization, Sodium Lauroyl Sarcosinate (HAMPOSYL L- 30, Chem/Serv, Minneapolis, MN) was aseptically added to the homogenized bacterial suspension for solubilization. The amount of Sarcosine (30%) added equaled 0.0664 times the solubilizing volume, in liters, (1.0 gram sarcosine/4.5 grams pellet mass). The process tank was removed from the homogenizer and kept at 4° C. while stirring at 240 rpm for 60-70 hours.

Protein harvest: The insoluble proteins within the solubilized process fluid were collected by centrifugation using T-1 SHARPLES, (Alfa Laval Seperations, Warminster, PA). Briefly, the solubilized homogenate was fed into six SHARPLES with a feed rate of 250 ml/minute at 17 psi at a centrifugal force of 60,000 x g. The temperature during centrifugation was kept at 4° C. The solubilized homogenate was passed 2 times across the centrifuges. The protein was collected, resuspended and dispensed in 10 liters Tris-buffer pH 8.5 containing 0.3% formalin (Sigma) as preservative.

Diafiltration: The protein suspension (10 liters) was adjusted to 60 liters using sterile Tris-buffer, pH 8.5. The suspension was washed and dialyzed using a MILLIPORE PELLICON Tangential Flow Filter assembly (Millipore Corporation), equipped with a 25ft$^2$ screen-channel series ALPHA 10K CENTRASETTE filter (Pall Filtron) to remove residual sarcosine. The protein solution was concentrated by filtration to a target volume of 10 liters at which point 50 liters of Tris-buffer pH 7.4 containing 5% isopropyl alcohol was slowly added to the concentrate from a second process tank. Isopropyl alcohol is thought to cause a slight unfolding of the protein structure allowing for the removal of bound sarcosine without compromising the immunogenicity of the proteins. Diafiltration continued until the pH stabilized to 7.4 at which point 50 liters Tris-buffer pH 7.4 was slowly added by diafiltration to remove residual alcohol. The protein suspension was then concentrated to approximately 5 liters. The protein concentrate was equally dispensed (500 ml) into ten sterile 1liter Nalgene containers and stored at -20° C. until use.

Example 3

Analysis of Proteins

Figure 3:
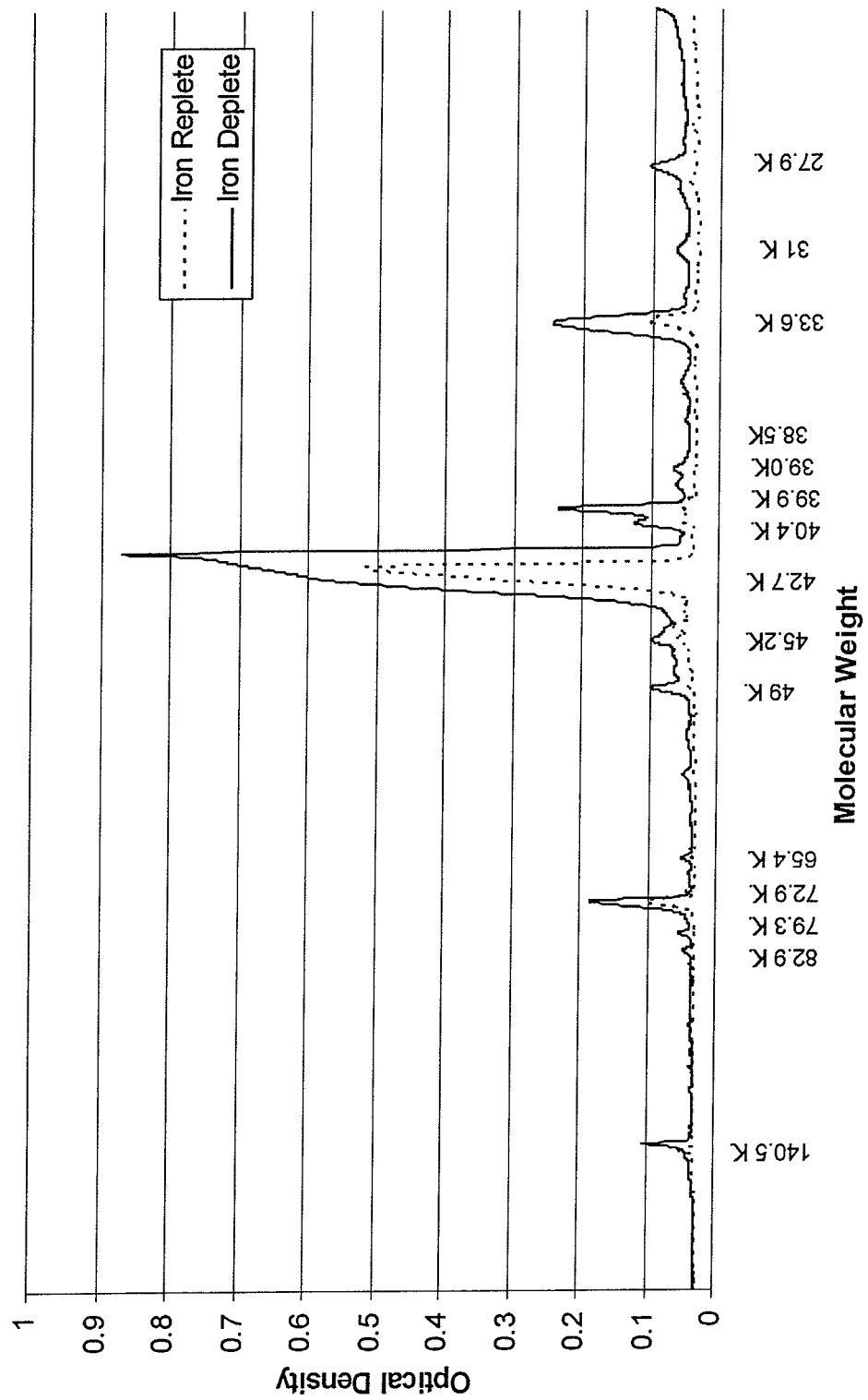
FIG. 3. Gel-image of membrane proteins derived from *F. necrophorum* grown under iron-replete and iron-depleted growth conditions.

The protein profile of the F. necrophorum subsp. necrophorum isolate grown in iron-replete and/or iron-deplete media was examined by SDS-PAGE. Briefly, the organism was grown from a frozen master seed stock by sub-culturing into 25 ml of P-BHI containing 0.05% cysteine (sigma) and 15 to 20 micrograms per milliliter (μg/ml) of 2,2-dipyridyl (Sigma-Aldrich St. Louis, MO) and/or P-BHI containing 200 uM ferric chloride incubated for 18 hours at 37° C. while stirring at 100 rpm. At 18 hours of incubation, 5 ml of each culture was transferred into 500 ml of pre-incubated (37° C.) iron-deplete and/or iron-replete media. Cultures were allowed to grow for 18 hours at 37° C. while stirring at 100 rpm. At 18 hours post incubation each culture was centrifuged at 10,000 x g for 20 minutes. The bacterial pellet was resuspended in a 100 ml of Tris-buffered saline and centrifuged at 10,000 x g for 10 minutes to remove any contaminating media proteins. The bacterial pellet from the iron-replete and iron-deplete media was resuspended in 40 ml of Tris-buffered saline pH 7.2 and disrupted by sonicaton. The disrupted bacterial suspension was clarified by centrifugation at 32,000 x g for 12 minutes. The supernatant was collected and solubilized by the addition of sodium lauroyl sarcosinate 4% vol/vol at 4° C. for 24 hours. The insoluble proteins were collected by centrifugation at 32,000 x g for 2.5 hours at 4° C. The OMP pellet was resuspended in 200 μl Tris-buffer at pH 7.2 and stored at -90° C. A sample of each extract was resolved on a 10% SDS-PAGE gel to compare the protein profiles. The gel was scanned using a BIORAD GS- 800 densitometer to compare the difference in the protein profile of F. necrophorum grown under iron-replete and iron-deplete conditions. The scanned gel is shown in FIG. 3.

The electrophoretic banding profiles of the proteins isolated from the Fusobacterium necrophorum isolate grown in the following three conditions were compared: iron-replete media (500 mls P-BHI containing 50 μM ferric chloride), iron-deplete media (500 ml P-BHI containing 15 μg 2,2-dipyridyl and 0.05% cysteine), and controlled fermentation conditions (the iron-deplete fermentation conditions of Example 2). The results revealed identical banding profiles between each sample grown under iron-deplete conditions. A number of metal regulated proteins were observed with molecular weights of approximately 82.9 kDa, 79.3 kDa, 65.4 kDa, 49 kDa, 39 kDa, 38.5 kDa, 31 kDa, and 27.9 kDa and non-iron regulated proteins having molecular weights of approximately 45.2 kDa, 40.4 kDa, 39.9 kDa, and 33.6 kDa. A number of metal regulated proteins having molecular weights of approximately 140.5 kDa, 72.9 kDa, 42.7 kDa, and 33 kDa appeared to be enhanced or up-regulated when grown under iron-deplete conditions as compared to the same band expressed under iron-replete conditions.

Example 4

Protein Expression by Field Isolates

To determine if differences exited in the banding profiles between field isolates of Fusobacterium the following study was undertaken. Bovine livers were collected from numerous commercial butchers having large necrotic foci. Each foci was sub-cultured anaerobically on blood agar plates. Colonies believed to be Fusobacterium spp. were isolated and characterized chemically and nutritionally using API 20-A identification test kits (Biomerieux, Marcy l'Etoile, France). Six isolates (isolates 1248, 1250, 1251, 1252, 1253, and 1255) were collected and identified as Fusobacterium necrophorum/nucleatum. Isolates were grown as described in Example 3, and a sample of each extract was resolved on a 10% SDS-PAGE gel to compare the protein profile obtained from each isolate grown in iron-replete and iron-deplete media. The gel was scanned using a BIORAD GS-800 densitometer to compare the difference in the protein profile of the isolates grown under iron-replete and iron-deplete conditions. The results revealed identical banding profiles between each isolate grown under iron-deplete conditions. A number of metal regulated proteins were observed with molecular weights of approximately 82.9 kDa, 79.3 kDa, 65.4 kDa, 49 kDa, 39 kDa, 38.5 kDa, 31 kDa, and 27.9 kDa and non-iron regulated proteins having molecular weights of approximately 45.2 kDa, 40.4 kDa, 39.9 kDa, and 33.6 kDa. A number of other bands having molecular weights of approximately 140.5 kDa, 72.9 kDa, 42.7 kDa, and 33 kDa appeared to be enhanced or up-regulated when grown under iron-deplete conditions as compared to the same band expressed under iron-replete conditions. The banding profiles of natural field isolates of Fusobacterium appeared not to vary from the ATCC isolate of example 3. This was surprising and unexpected in view of the differences in putative iron uptake systems recently observed between 2 *Fusobacterium* spp (Kapatral et al., Genome Res., 13, 1180-1189 (2003).

Example 5

Preparation of the Immunizing Compositions Derived from *Fusobacterium necrophorum*

The composition made from *F. necrophorum* as described in example 1 was used to prepare a vaccine. A stock vaccine was prepared from the composition by diluting the antigen into phosphate buffered saline (PBS) containing 8.0 g/l NaCl, 0.2 g/l KCl, 1.44g/l $Na_2HPO_4$ and 0.24g/l $KH_2PO_4$ pH 7.4 containing 10% aluminum hydroxide (REHYDRO-GEL, Reheis Chemical Company Berkeley Heights, NJ). The aluminum hydroxide suspension (500 μg total protein/ml) was then emulsified into the commercial adjuvant, EMULSIGEN, (MVP Laboratories, Ralston, Nebraska) using a EKA ULTRA TURRAX T-50homogenizing vessel (IKA, Cincinnati, OH). A mouse dose was administered to give a final dose of 50 μ total protein in a 0.1 ml injectable volume with an adjuvant concentration of 22.5% vol/vol. A placebo was prepared by replacing the antigen with physiological saline in the above formulation and emulsifying the suspension into EMULSIGEN to give an adjuvant concentration of 22.5%.

Example 6

Mouse Vaccination

The efficacy of the *Fusobacterium necrophorum* vaccine was carried out against a live virulent challenge in mice. Thirty (N=30) female CF-1 mice obtained from Harlan Breeding Laboratories (Indianapolis, Ind.) weighing 16-22 grams were equally distributed into two groups (15 mice/group). Mice were housed in polycarbonate mouse cages (Ancore Corporation, Bellmore, N.Y.). Groups were designated as Group-1 (Placebo) and Group-2 (Vaccinated). Food and water was supplied *ad libitum* to all mice. Mice were vaccinated intraperitoneally three times at 14 day intervals. The volume administered was 0.1 ml/mouse.

Example 7

Preparation of Challenge Organism

The *F. necrophorum* isolate as described above was used for challenge. Briefly, the isolate from a frozen stock (example 1) was streaked onto a blood agar plate and incubated at 37° C. for 18 hours. Several colonies were sub-cultured into 50 ml P-BHI containing 15 μg/ml 2,2' dipyridyl and 0.05% cysteine. The culture was incubated at 37° C. for 16 hours, and then centrifuged at 10,000×g for 10 minutes at 4° C. to pellet the bacteria. The bacterial pellet was washed once by centrifugation (10,000×g for 15 minutes) at 4° C. The final pellet was resuspended in 25 ml of P-BHI without dipyridyl. Just prior to challenge, 1 ml of the above bacterial suspension was serially diluted ten fold to enumerate the number of CFU/dose.

Example 8

Challenge

Fourteen days after the third vaccination, mice in groups 1 and 2 were intraperitoneally challenged with 0.1 ml of *F. necrophorum* ($3.0\times10^8$ colony forming units) prepared as described in example 6. Mortality was recorded daily for 4 days after challenge. At four days post challenge the experimental trial was terminated. All surviving mice from each group were euthanized by carbon dioxide. The liver from each mouse was aseptically removed and gross examination was done to determine differences in necrotic foci. The entire right lobe of each liver was then macerated, individually weighted and adjusted to give a 1:10 dilution weight: volume per sample. Each sample was serially diluted ten fold and plated in duplicate on blood agar plates to enumerate the difference in the number of F. necrophorum bacteria per liver between groups.

Results

The results showed a strong protective index against a systemic challenge as seen in Table 1, and FIG. 1. Twelve out of 15 (80.0%) of the placebo-vaccinated mice (Group 1) died within 4 days after challenge. In contrast, only 4 mice out of 15 (26.7%) died in Group 2 (degree of significance of P=0.0046).

TABLE 1

Mortality of Vaccinated and Non-Vaccinated Mice Following IP Challenge with *Fusobacterium necrophorum*

| Treatment Groups | # Mice | # Dead | [a]Percent mortality (%) |
| --- | --- | --- | --- |
| Group 1 (Placebo) | 15 | 12/15 | 80.0 |
| Group 2 (Vaccinated) | 15 | 4/15 | 26.7 |

[a]The percent of mice that died 4 days after IP challenge with $3.0 \times 10^8$ cfu of *F. necrophorum*. The degree of significance of mortality between the vaccinated group compared to the placebo group was P = 0.0046 as determined by Fisher Exact Test.

Figure 2:
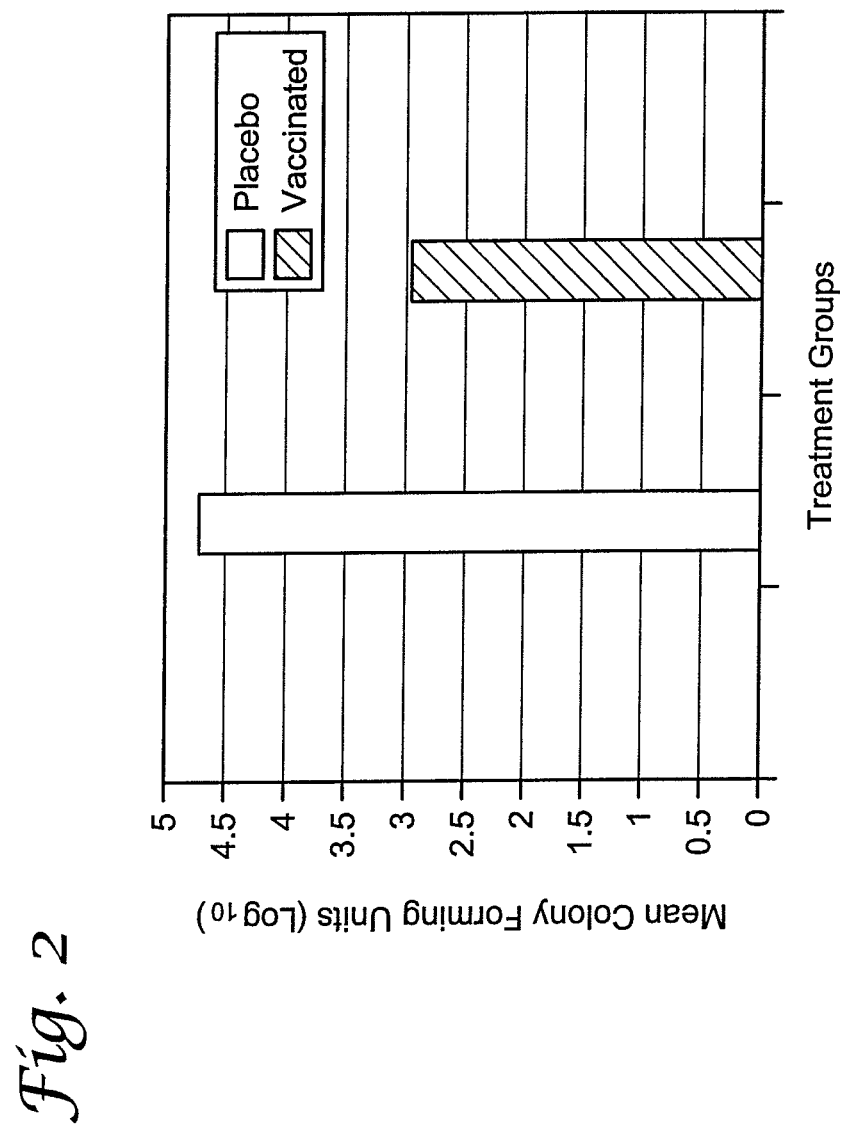
FIG. 2. Recovery of *F. necrophorum* in livers of vaccinated and control mice after intraperitoneal challenge.

Gross examination of each liver revealed a dramatic difference in the number of visible necrotic plaques between the Placebo and Vaccinated mice. It was clearly evident that mice given the vaccine rapidly reduced the number of bacteria able to proliferate successfully in the systemic circulation as indicated by the reduction in visible necrotic foci as compared to the placebo vaccinated mice. This is further substantiated in the results comparing the difference in the quantitative clearance of *F. necrophorum* from the livers between the vaccinated and Placebo vaccinated mice as seen in FIG. 2. The difference in the number of bacteria in the livers of Placebo vaccinated controls and the vaccinated group was highly statistically significant (degree of significance of P=0.041), suggesting greater quantitative clearance of *F. necrophorum* in the livers of vaccinated mice. The mean colony forming units expressed as $log_{10}$ was 4.72 in the placebo vaccinated group as compared to an average log count of 2.97 in the vaccinated group. This is a 95% reduction in the number of bacteria in the vaccinated group when compared to the Placebo group.

The vaccine composition showed a high degree of systemic protection as compared to non-vaccinated mice of Group 1 (Placebo vaccinated). The vaccine prepared from *F. necrophorum* was highly efficacious in preventing mortality associated with a lethal *F. necrophorum* challenge in a standardized mouse model as well as reducing the formation of necrotic foci and the number of colony forming units in the liver.

Example 9

Decreased Blood Culture of *Fusobacterium necrophorum* after Intravenous Challenge Comparing Vaccinated to Non-Vaccinated Holstein Steers The purpose of this study included evaluating the ability of the composition derived from *F. necrophorum* to decrease the number of colony forming units of the challenge organism in blood. The immunizing composition was prepared from *F. necrophorum* as described in Example 5, except for the following modification; a bovine dose was calculated to give a final dose of 1000 ug total protein in a 2 ml injectable volume (500 ug/ml).

Six steers (N=6) with an average weight of approximately 300 pounds were randomly distributed into a single pen. Steers were ear tagged for identification and randomly allocated into two groups designated as groups 1 and 2 (3 steers/treatment group). Steers in group 1 were designated as non-vaccinated and remained as the non-vaccinated control group. Steers in groups 2 were vaccinated two times at 14 day intervals. The efficacy of the composition was evaluated by collecting data on the following outcome parameters: 1) the potency of the immunizing composition was evaluated in its ability to decrease the number of colony forming units of *F. necrophorum* in blood after intravenous challenge compared to non-vaccinated steers, 2) the comparison of clinical morbidity between vaccinates and non-vaccinates and 3) histopathogical changes in the livers between vaccinated and non-vaccinated steers.

Example 10

Blood Sample Collection

Blood samples were collected from all steers at time of first vaccination (Pre-exposure); 14 days after 2 vaccination (hyperimmunized) and again 14 days after challenge. Blood collected from non-vaccinated steers at 14 days after challenge was designated convalescent sera, and blood collected from the vaccinated steers at 14 days after challenge was designated vaccinated/challenged sera. All blood was collected in sterile 13×75 millimeter vacutainer collection tubes (SST No. 369783, Becton Dickinson, Franklin Lakes, N.J.). After clotting the blood tubes were centrifuged at 800×g for thirty minutes and frozen at −20° C.

Example 11

Challenge

Fourteen days after the second vaccination, steers in groups 1 and 2 were intravenously challenged with 1.0 ml of *F. necrophorum* (2.4 x $10^8$ colony forming units) prepared as described in example 7. Blood samples were collected at 4, 12 and 24 hours after intravenous challenge to enumerate the number of colony forming units of Fusobacterium between vaccinates and non-vaccinates. Briefly, a 10ml sample of blood was collected from the jugular vein from each steer at 4, 12 and 24 hours post challenge and immediately placed into 90 ml of BBL SEPTIC-CHECK COLUMBIA blood culture broth (Becton Dickinson, MD). Each sample was serially diluted ten fold and plated in duplicate on blood agar plates to enumerate the difference in the number of *F. necrophorum* bacteria per milliter of blood between experimental groups.

Figure 4:
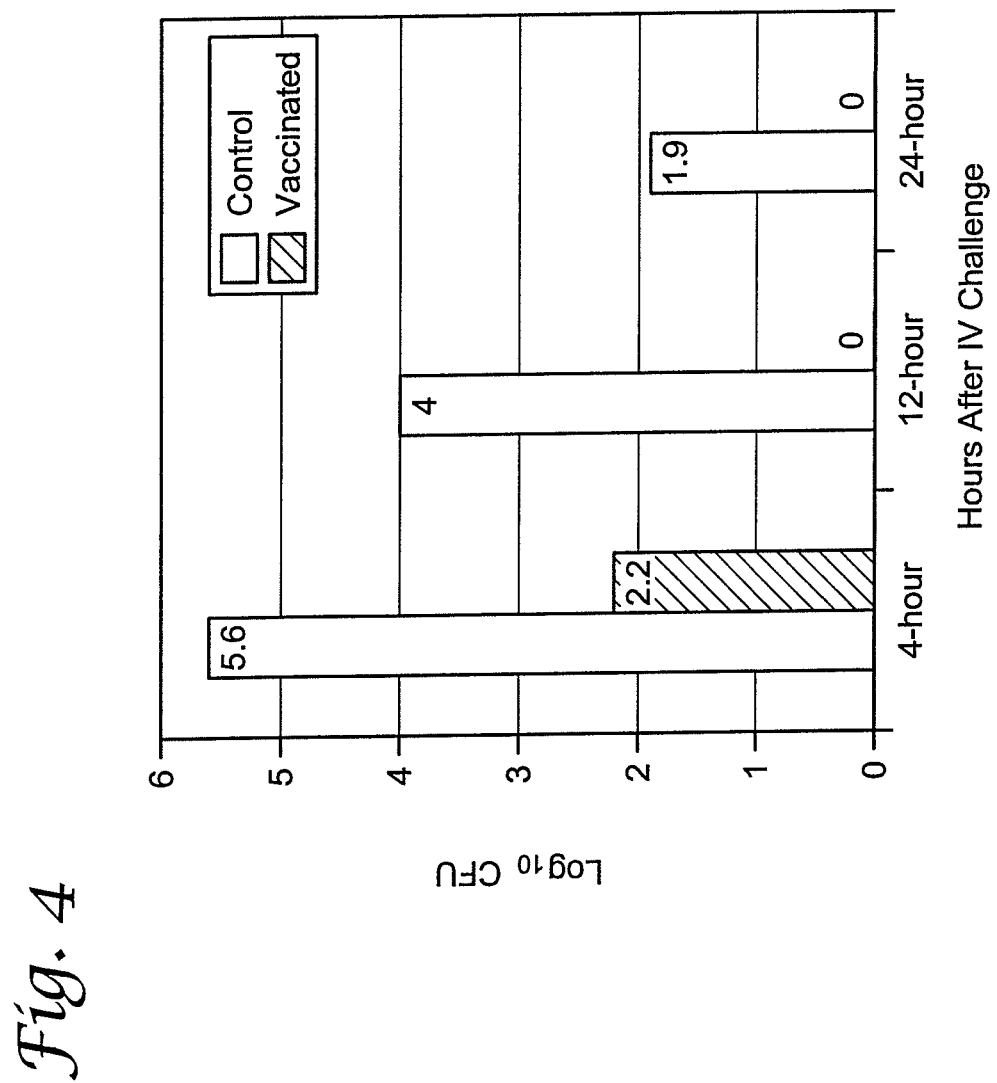
FIG. 4. Decreased isolation of *F. necrophorum* from blood samples in vaccinated and control Holstein steers following intravenous challenge.

At 4, 12 and 24 hours post challenge it was clearly evident that the vaccine rapidly reduced the number of *F. necrophorum* bacteria able to proliferate successfully in the systemic circulation of vaccinated steers when compared to the non-vaccinates (Table 2, FIG. 4).

TABLE 2

Decreased Blood Culture of *Fusobacterium necrophorum*[a] after intravenous Challenge Comparing Vaccinated to Non-Vaccinated Holstein Steers

| | $Log_{10}$ CFU of *F. necrophorum* | |
|---|---|---|
| Hours Post Challenge | Group 1 (Non-Vaccinated) | Group 2 (Vaccinated) |
| 4 hours | 5.6 | 2.2 |
| 12 hours | 4.0 | 0 |
| 24 hours | 1.9 | 0 |

[a]The decrease in the Number of Colony Forming Units of *Fusobacterium necrophorum* after intravenous challenge with 2.4 x $10^8$ CFU of *F. necrophorum* comparing the efficacy of vaccinated steers to non-vaccinated controls.

As indicated by the reduction in the number of colony forming units of the challenge organism at each sampling period, the results clearly demonstrate that the composition was highly efficacious. The results show that vaccination reduced the number of infective organisms able to proliferate successfully in the systemic circulation of the host. This decrease in the infective dose would also decrease the ability of the organism to induce clinical disease or manifest clinical symptoms primarily by reducing the systemic burden of the infective organism. This is clearly seen in table 1 and FIG. 4.

Example 12

Morbidity

Steers in groups 1 and 2 were visually observed daily for 21 days after challenge for clinical abnormalities or signs of disease. During the observation period none of the vaccinated steers showed any clinical signs and/or symptoms of disease. In contrast, all of the non-vaccinated steers were visibly affected by the intravenous challenge. Within 24 hours after challenge non-vaccinates withdrew from feed and water and became lethargic, less aggressive and depressed. Within one week post challenge all non-vaccinated steers began to show a high degree of lameness characterized by reduced activity in rising and moving with the adoption of unusual or abnormal posture, to include, limpness, sagging, stiffness, and lack of flexion particularly in the fetlock and hock joints. Within fourteen days post challenge all non-vaccinated steers were having great difficulty walking and/or standing erect. Again these observations correlate well with the observed ability of the vaccine to decrease the challenge burden of the infective dose systemically, thus preventing the spread of the challenge organism to multiple tissue sites.

Example 13

Termination of Trial and Conclusion

At 21 days post intravenous challenge the calves were euthanized by lethal injection and the trial terminated. During this time period the non-vaccinated steers never regained their health status as compared to the vaccinated steers. Upon visual and gross examination the vaccinated steers were heavier in body weight as compared to their non-vaccinated cohorts. The results showed a positive difference in weight due to vaccination presumably due to controlling infectivity of the challenge organism.

Post mortem examination revealed no abnormal differences in the internal organs. The livers were removed and examined for necrotic foci by dissection. No visible necrotic foci or lesions could be observed in any of the livers upon gross examination. Each liver was dissected and sections removed for histological examination to determine if any tissue abnormalities or changes due to the intravenous challenge could be observed between vaccinated and non-vaccinated steers. Hepatic examination of hematoxylin-and-eosin stained liver sections reveals microscopic changes in non-vaccinated controls. Non-vaccinated steers show a range of pathologies, from small foci of lymphocyte inflammation to pronounced foci with necrosis and hemorrhage. Hepatic abscesses may be large enough to be observable by visual observation if an infection is allowed to continue. Such pathologies are not typically observed in the vaccinated steers.

These results clearly demonstrate that vaccination with the composition as described in Examples 8 and 10 decreased the burden of the challenge organism systemically which reduced the overall morbidity of disease and lessened hepatic necrosis of the liver.

Example 14

Figure 5:
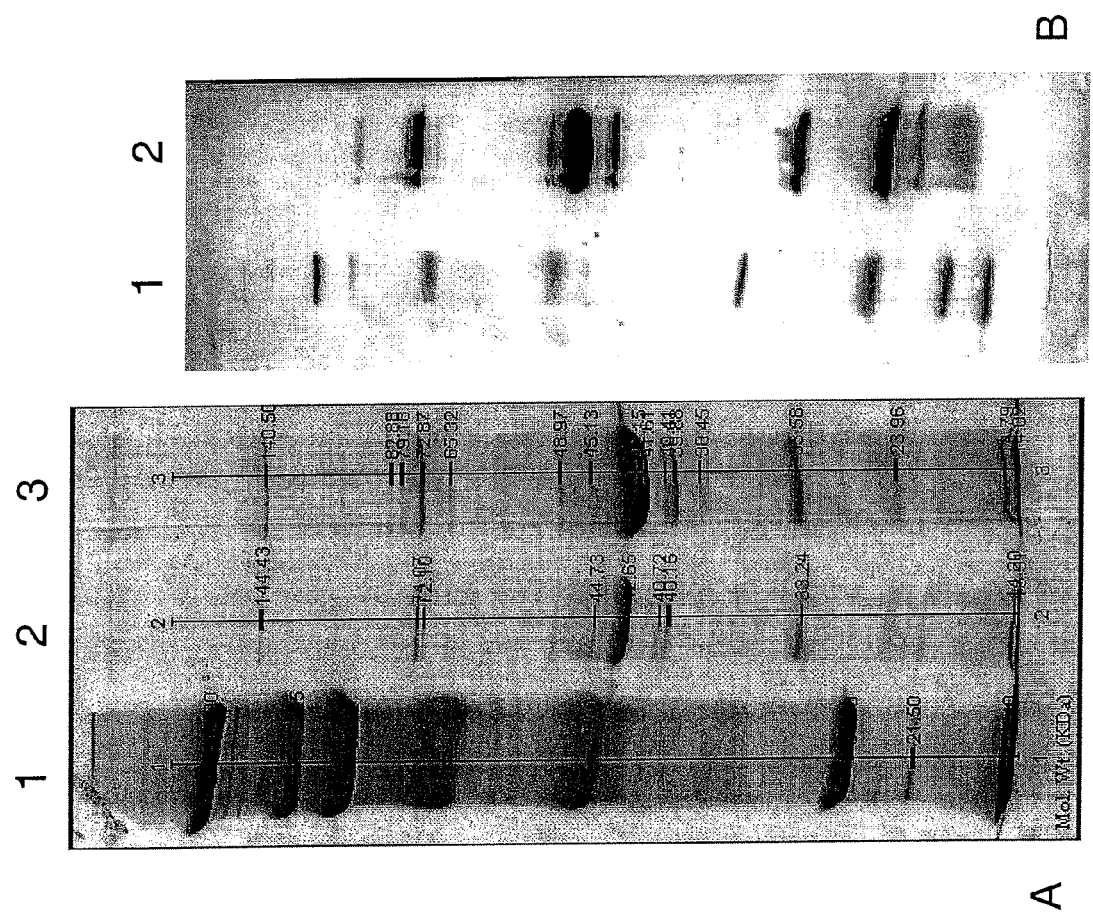
FIG. 5. A. *F. necrophorum* resolved on SDS-polyacrylamide gel and stained with Coomasi Brilliant Blue. Lane 1, molecular weight markers; lane 2, *F. necrophorum* grown in iron replete media; lane 3, *F. necrophorum* grown in iron depleted media. The molecular weights of some proteins are shown in lanes 2 and 3. B. Western immunoblot of the *F. necrophorum*. Lane 1, molecular weight markers; lane 2, *F. necrophorum* grown in iron depleted media.

Identification of Sero-Reactive Membrane Proteins of *F. necrophorum* Using Western blot Analysis The proteins in the vaccine composition as described in Example 5 were subjected to electrophoresis followed by western blot analysis with hyperimmunized serum as described in Example 10. Briefly, the membrane proteins derived from *F. necrophorum* grown under iron-limiting conditions were size-fractionated on an SDS-PAGE gel using a 4% stacking gel and 10% resolving gel. A 10 μ sample was combined with 30μl of SDS reducing sample buffer (62.5 mM Tris-HCL ph 6.8, 20% glycerol, 2% SDS, 5% β-mercaptoethanol) and boiled for 4minutes. Samples were electrophoresed at 18 mA constant current for 5 hour at 4° C. using a PROTEIN II xi cell and model 1000/500 power supply (BioRad Laboratories, Richmond, CA). Band migration was visualized using broad range kaleidoscope standards (BioRad) to aid in the electro-blot transfer while biotinylated broad range standards were used as molecular weight references on the blot, see FIG. 5. For Western blot analysis, proteins were electroblotted from the gel onto trans-blot nitrocellulose membranes (BioRad) overnight, at 4° C. at 50 V, in Towbin buffer (25 mM Tris, 192 mM glycine, 20% methanol) using a BIORAD TRANS-BLOT transfer cell and a PAC 300 power supply (BioRad). The nitrocellulose membrane was blocked using 3% fish gelatin (Sigma Chemical, St. Louis, Mo) in Tris buffered saline (TBS- 20 mM Tris, 500 mM NaCl, pH 7.5) for 1 hour while shaking at 37° C. The membrane was dried at 37° C. and blocked in TBS containing 3% fish gelatin and this process was repeated. The membrane was then probed with the polyclonal hyperimmunized sera collected from the immunized steers as described in example 10. The primary antibody was diluted 1/2500 in TBS containing 1% fish gelatin, 0.05% Tween 20 and 0.2% sodium azide (Antibody Buffer). The membrane was incubated with the primary antibody solution overnight on a shaker at room temperature. The membrane was then washed two times in TBS containing 0.05% Tween 20 (TTBS) and transferred to antibody buffer containing a 1/10,000 dilution of Alkaline phosphatase-conjugated mouse anti-bovine IgG clone BG-18 (Sigma) and a 1/3000dilution of avidin conjugated to alkaline phosphatase (BioRad). The membrane was incubated at 37° C. for 2 hours on a shaker, then washed in TTBS four times to remove unbound conjugate. The blot was resolved in substrate solution containing alkaline phosphate color reagent A and B in 1× AP color development Buffer (BioRad) for 30 min. at 37° C. on a shaker. The resulting Western immunoblot was documented using a BIORAD GS-800 Densitometer (see FIG. 5B).

The purpose of this analysis was to determine which of the proteins present in the immunizing composition induced antibody responses following immunization of steers. The results revealed immunological reactivity with bands at the 82.9 kDa, 65.4 and the 49 kDa region as well as bands within the range of 45.2 kDa-38.5 kDa and 31 kDa-27.9 kDa. These results demonstrated that the membrane proteins of the composition described in Example 3 reacted strongly with the hyperimmunized sera described in Example 10, suggesting that these components of the vaccine may provide protection against disease. The remaining proteins of approximate molecular weights (in kDa) of 140.5, 72.9, 42.7, 40.4, 39.9, 33.6, and 33 did not show reactivity to the hyperimmunized sera. However, the sensitivity limits of the assay may have prevented the detection of weaker interactions, that, although less evident, may still contribute to the vaccine's effectiveness by augmenting the immune response to the composition. In addition, the proteins that were not sero-reactive in this assay may elicit responses other than antibody production, such as stimulation of cytokines, interferon, interleukins, T-cells, or colony-stimulating factors. Such responses could enhance, direct, or restore the ability of the host's immune system to fight disease.

Example 15

Methods for the Identification of Membrane Proteins Derived from *Fusobacterium* Using Reversed-Phase High-Pressure Liquid Chromatography The vaccine composition described in Examples 1 and 5 consists of multiple membrane proteins derived from *Fusobacterium* grown under iron-restricted conditions. In order to identify which proteins are efficacious within the composition, experiments were conducted to separate these proteins to test their individual antigenicity. Traditional two-dimensional electrophoresis was initially investigated in our laboratory as a method of separating the membrane proteins derived from gram-negative bacteria grown under iron-limiting conditions. The method proved to be of limited success since many of the large membrane proteins could not be separated by this method. To achieve better separation of the proteins and further clarification of target vaccine antigens, methods for utilizing Reversed-Phase High-Pressure Liquid Chromatography (RP-HPLC) based on hydrophobicity were standardized and have been used to separate the membrane proteins derived from *Fusobacterium* and other gram negative bacteria grown under iron-restricted conditions. Briefly, membrane proteins were prepared as described in Example 1. Proteins were solubilized in membrane solubilization buffer (5 M urea, 2 M thiourea, 10% glycerol, 2.5% w/v N-decyl-N,N-dimethyl-3-ammonio-1-propane sulfonate, 50 mM Tris, 2% n-octylglucoside, 5 mM Tris-(carboxyethyl) phospine hydrochloride, 1 mM protease inhibitor) for 24 h at 4° C. To separate the proteins, a two-dimensional liquid chromatography (2-D LC) method was used. The first dimension was chromatafocusing LC, using a HPCF-1D column (Eprogen, Darien, IL) and a SYSTEM GOLD HPLC (Beckman Coulter, Buckinghamshire, England). The pH gradient was generated using a starting buffer (SB) and an elution buffer (EB). The SB consisted of 6 M urea and 25 mM Bis-Tris, adjusted to pH 8.5 with iminodiacetic acid. The EB consisted of 6 M urea, 10% Polybuffer™74 (Amersham Biosciences), adjusted to pH 4.0 with ammonium hydroxide. Prior to applying sample, the HPCF-1D column was prepared by a 1-hour wash with water followed by equilibration with 10volumes of SB until the pH of the effluent was 8.5. The sample was then applied, and a pH gradient was established by adding EB to the column at 0.2 mL/min. The pH of the mobile phase effluent was monitored online using a postdetector pH flow cell with a dead volume of about 150µL. Fractions were collected every 0.3 pH unit using a fraction collector. A total of 26 fractions were collected from the chromatofocusing column. Separations were monitored by measuring the absorbance (at 280 nm) of eluted fractions. The second dimension of 2-D LC is nonporous reversed-phase HPLC. Separations were performed with a RP-HPLC column packed with 1.5 uM nonporous C-18 silica beads (ODS-IIE, Eprogen) with a flow rate of 700 µ/min. A gradient of two solvents were used. Solvent A consisted of nanopure water with 0.1% trifluoroacetic acid (TFA), and Solvent B consisted of acetonitrile (ACN) with 0.08% TFA. The gradient was accomplished by the following schedule: 5-25% solvent B in 1 min; 25-31% B in 1 min; 31-37% B in 8 min, 37-41% B in 8 min; 41-67% B in 8 min; 67-100% B in 2 min; 100% B for 1min, and 100-5% B in 1 min. Elution profiles were monitored at 214 mn. Fractions were collected and stored at -90° C. in 96 well micro-titer plates.

Example 16

Target Antigen Screening of RP-HPLC Fractions Using dot-ELISA

Each fraction will be screened for potential vaccine target antigens using a 96-well dot-ELISA. Briefly, bovine sera derived from *Fusobacterium* convalescent, hyperimmunized, vaccinated/challenged and challenged only steers will be used to screen individual fractions as described in Example 15. Nitrocellulose membranes (1620117, 0.45um BioRad, Richmond CA) are washed with Tris-buffered saline (TBS) for 5 minutes and blotted with #5 Whatman paper to remove excess TBS. The nitrocellulose membrane is then placed into a BIO-DOT 96 well manifold (Bio-Rad). Fractions (2 ul) as described in example 15 are carefully dotted into each well (duplicate samples) and allowed to dry at room temperature. After drying the nitrocellulose membrane is blocked using 4% fish gelatin (Sigma Chemical Co, St. Louis, MO) prepared in TBS to block non-specific binding sites. The membrane is incubated at 37° C. while constantly stirring at 100 rpm on a platform shaker. After incubation the blocking mixture is aspirated and the wells washed 4 times with TBS containing 0.05% Tween-20 and 1% fish gelatin. Sera diluted 1:200 will be added (100 ul) to each well. The membrane is incubated for 1hour at 37° C., at which point the serum is aspirated off and the membrane washed 4 times. Alkaline phosphatase-conjugated mouse anti-bovine IgG clone BG-18 (Sigma) optimally diluted is added to each well (100 ul), then incubated for 2 hours at 37° C. while stirring at 100 rpm. The conjugate solution is aspirated and the wells washed 4 times. PnPP substrate (Sigma) prepared in 0.1 M glycine buffer is added to each well (100 ul). The substrate is allowed to react for 45minutes at 37° C. The membrane is removed and the reaction terminated by immersing in 3 N NaOH. The membrane is scanned using a BIORAD GS-800 densitometer to evaluate which fractions reacted with the hyperimmunized sera or gave a positive reaction as defined as a colored dot. Fractions giving positive reactions are recorded and each protein further identified by peptide mass fingerprinting with MALDI-TOF-MS.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A composition comprising an isolated whole cell preparation of a *Fusobacterium* spp., wherein the cells comprise at least two meta regulated polypeptides having molecular weights between 76 kDa and 86kDa, between 62 kDa and 68 kDa, between 45 kDa and 53 kDa, between 34 kDa and 43 kDa, or between 24 kDa and 35 kDa, wherein molecular weight is determined by eiectrophoresis on a sodium dodecyl sulfate-polyacrylamide gel, wherein the metal regulated polypeptides are natively expressed by a *Fusobacterium* spp. when incubated in medium that includes a metal chelator and not natively expressed at a detectable level when grown in the medium in the absence of a metal chelator and further comprising an adjuvant.

2. The composition of claim 1 wherein the *Fusobacterium* spp. is *F. necrophorum* or *F. nucleatum*.

3. The composition of claim 1 wherein the *Fusobacterium* spp. is the *F. necrophorum* strain deposited with the American Type Culture Collection (ATCC) and given ATCC Accession No. PTA-10318.

4. The composition of claim 1 wherein the composition does not comprise a polypeptide having leukotoxin activity.

5. The composition of claim 1 wherein each of the at least two metal regulated polypeptides has a molecular weight between 78 kDa and 84 kDa, between 64kDa and 66 kDa, between 47 kDa and 51 kDa, between 36 kDa and 41kDa, or between 27 kDa and 32 kDa.

6. The composition of claim 1 wherein each of the at least two metal regulated polypeptides has a molecular weight of 83 kDa, 79 kDa, 65 kDa, 49 kDa, 39kDa, 31 kDa, or 28 kDa.

7. The composition of claim 1 wherein the cells further comprise at least one polypeptide having a molecular weight of between 136 kDa and 144 kDa, between 69 kDa and 77 kDa, between 39 kDa and 47 kDa, or between 29 kDa and 37 kDa, and natively expressed by a *Fusobacterium* spp. when grown in medium with or without a metal chelator, wherein expression of the polypeptide is enhanced during growth in the medium with the metal chelator.

\* \* \* \* \*

UNITED STATES PATENT AND TRADEMARK OFFICE
CERTIFICATE OF CORRECTION

PATENT NO.       : 9,487,564 B2  
APPLICATION NO.  : 12/108920  
DATED            : November 8, 2016  
INVENTOR(S)      : Darren E. Straub and Daryll A. Emery Page 1 of 1

It is certified that error appears in the above-identified patent and that said Letters Patent is hereby corrected as shown below:

In the Claims

Column 28, Line 51:  
Delete "meta" and  
Insert --metal--

Column 28, Line 55:  
Delete "eiectrophoresis" and  
Insert --electrophoresis--

Signed and Sealed this  
Twelfth Day of September, 2017

Joseph Matal  
*Performing the Functions and Duties of the*  
*Under Secretary of Commerce for Intellectual Property and*  
*Director of the United States Patent and Trademark Office*